(12) United States Patent
Anderson et al.

(10) Patent No.: US 12,310,965 B2
(45) Date of Patent: May 27, 2025

(54) TREATMENT OF CANCER UTILIZING AN IDENTIFIED ADENOSINE FINGERPRINT

(71) Applicant: ARCUS BIOSCIENCES, INC., Hayward, CA (US)

(72) Inventors: Amy Elizabeth Anderson, San Mateo, CA (US); Devika Ashok, Belmont, CA (US); Daniel M. DiRenzo, Palo Alto, CA (US); Akshata R. Udyavar, Foster City, CA (US); Matthew J. Walters, Pacifica, CA (US); Stephen W. Young, Palomar Park, CA (US)

(73) Assignee: ARCUS BIOSCIENCES, INC., Hayward, CA (US)

( * ) Notice: Subject to any disclaimer, the term of this patent is extended or adjusted under 35 U.S.C. 154(b) by 844 days.

(21) Appl. No.: 17/599,472

(22) PCT Filed: Mar. 27, 2020

(86) PCT No.: PCT/US2020/025242
§ 371 (c)(1),
(2) Date: Sep. 28, 2021

(87) PCT Pub. No.: WO2020/205527
PCT Pub. Date: Oct. 8, 2020

(65) Prior Publication Data
US 2022/0211701 A1  Jul. 7, 2022

Related U.S. Application Data

(60) Provisional application No. 62/826,728, filed on Mar. 29, 2019.

(51) Int. Cl.
| A61K 31/506 | (2006.01) |
| A61K 31/706 | (2006.01) |
| A61K 31/7076 | (2006.01) |
| A61K 45/06 | (2006.01) |

(52) U.S. Cl.
CPC .......... *A61K 31/506* (2013.01); *A61K 31/706* (2013.01); *A61K 31/7076* (2013.01); *A61K 45/06* (2013.01)

(58) Field of Classification Search
CPC ................ A61K 31/506; A61K 31/706; A61K 31/7076; A61K 45/06
USPC .......................................................... 514/47
See application file for complete search history.

(56) References Cited

U.S. PATENT DOCUMENTS

| 10,239,912 | B2 | 3/2019 | Debien et al. |
| 10,399,962 | B2 | 9/2019 | Beatty et al. |
| 10,981,944 | B2 | 4/2021 | Debien et al. |
| 11,001,603 | B2 | 5/2021 | Debien et al. |
| 11,072,597 | B2 | 7/2021 | Beatty et al. |
| 11,633,416 | B1 | 4/2023 | Lawson et al. |
| 2016/0129108 | A1 | 5/2016 | Sachsenmeier et al. |
| 2016/0153053 | A1 | 6/2016 | Skog et al. |
| 2017/0267710 | A1* | 9/2017 | Debien ................ C07H 19/207 |
| 2018/0125973 | A1 | 5/2018 | Sachsenmeier et al. |
| 2018/0200378 | A1 | 7/2018 | Bennett et al. |
| 2019/0022096 | A1 | 1/2019 | Willingham et al. |
| 2019/0031766 | A1 | 1/2019 | Prinz et al. |
| 2020/0405629 | A1 | 12/2020 | Jaen et al. |
| 2021/0371449 | A1 | 12/2021 | Debien et al. |
| 2021/0395291 | A1 | 12/2021 | Pennell et al. |
| 2021/0395391 | A1 | 12/2021 | Zhu et al. |
| 2022/0144808 | A1 | 5/2022 | Beatty et al. |
| 2022/0211701 | A1 | 7/2022 | Anderson et al. |
| 2022/0241313 | A1 | 8/2022 | Tan et al. |
| 2023/0382942 | A1 | 11/2023 | Pennell et al. |
| 2024/0352057 | A1 | 10/2024 | Debien et al. |

FOREIGN PATENT DOCUMENTS

| WO | WO-03/050241 A2 | 6/2003 |
| WO | WO-2004/079013 A1 | 9/2004 |
| WO | 2012031320 | 3/2012 |
| WO | WO-2015/031320 A1 | 3/2015 |
| WO | WO-2016/075099 A1 | 5/2016 |
| WO | WO-2016075176 | 5/2016 |
| WO | 2017040930 | 3/2017 |
| WO | WO-2017/120508 A1 | 7/2017 |
| WO | WO-2017/152085 A1 | 9/2017 |

(Continued)

OTHER PUBLICATIONS

Allard et al. Targeting the CD73-adenosine axis in immuno-oncology. Immunology Letters 205 (2019) 31-39. Available online May 24, 2018. (Year: 2018).*

Lupia et al. CD73 Regulates Stemness and Epithelial-Mesenchymal Transition in Ovarian Cancer-Initiating Cells. Stem Cell Reports vol. 10, p. 1412-1425, Apr. 10, 2018. Published: Mar. 15, 2018. (include Supplementary information, a total of 24 pages) (Year: 2018).*

"33rd Annual Meeting & Pre-Conference 2-9,16, Programs of the Society for Immunotherapy of Cancer (SITC 2018)", Journal for Immunotherapy of Cancer, Biomed Central Ltd, London, UK, vol. 6, No. 1, Nov. 6, 2018 (Nov. 6, 2018), pp. 1-205, XP021262326, DOI: 10.1186/S40425-018-0422-Y P35; p. 18.

(Continued)

*Primary Examiner* — Yih-Horng Shiao
(74) *Attorney, Agent, or Firm* — Sheppard Mullin Richter & Hampton LLP

(57) ABSTRACT

The present disclosure provides methods of treating a cancer in a subject having an established adenosine fingerprint. An established adenosine fingerprint includes assessing the blood concentration of one or more adenosine machinery proteins, assessing the enzymatic activity of one or more adenosine machinery proteins, and/or assessing the tumor expression level of adenosine machinery proteins. The methods disclosed herein include administering to said subjects a therapeutic agent selected from the group consisting of an agent targeting the extracellular production of adenosine, and an agent antagonizing the activation by adenosine of one of its receptors.

8 Claims, 18 Drawing Sheets

(56) References Cited

FOREIGN PATENT DOCUMENTS

| WO | WO-2018/067424 A1 | 4/2018 |
|---|---|---|
| WO | WO-2018/094148 A1 | 5/2018 |
| WO | WO-2018/136700 A1 | 7/2018 |
| WO | WO-2018/137598 A1 | 8/2018 |
| WO | WO-2018/187484 A1 | 10/2018 |
| WO | WO-2018/187508 A1 | 10/2018 |
| WO | WO-2018187512 | 10/2018 |
| WO | WO-2018/204661 A1 | 11/2018 |
| WO | WO-2018/213377 A1 | 11/2018 |
| WO | WO-2018/237173 A1 | 12/2018 |
| WO | 2019007140 | 1/2019 |
| WO | WO-2019/090347 A1 | 5/2019 |
| WO | WO-2019/161054 A1 | 8/2019 |
| WO | WO-2019/173682 A1 | 9/2019 |
| WO | WO-2019168744 | 9/2019 |
| WO | WO-2019/206872 A1 | 10/2019 |
| WO | WO-2019200256 | 10/2019 |
| WO | WO-2020/018680 A1 | 1/2020 |
| WO | WO-2020/023846 A1 | 1/2020 |
| WO | WO-2020/046613 A1 | 3/2020 |
| WO | WO-2020/123772 A1 | 6/2020 |
| WO | WO-2020/185859 A1 | 9/2020 |
| WO | WO-2021/138498 A1 | 7/2021 |

OTHER PUBLICATIONS

"Research 1-15, Poster Presentation Design 2015", Mar. 29, 2019 (Mar. 29, 2019), pp. 1-1, XP055972348, Retrieved from the Internet: URL:https://arcusbio.com/wp-content/uploads/2020/09/AACR-2019-Biomarkers-poster.pdf> the whole document.

Dipti Vijayan et al: "Targeting immunosuppressive adenosine in cancer", Nature Reviews Cancer, vol. 17, No. 12, Oct. 23, 2017 (Oct. 23, 2017), pp. 709-724, XP055557876, London, ISSN: 1474-175X, DOI: 10.1038/nrc.2017.86.

Direnzo Daniel et al: "Abstract 3168: Methods for assessment of the "adenosine fingerprint" in clinical trials of AB928", Cancer Research, vol. 79, No. 13_Supplement, Jul. 1, 2019 (Jul. 1, 2019), pp. 3168-3168, XP055972342, 2019 San Antonio Breast Cancer Symposium, San Antonio, Texas ISSN: 0008-5472, DOI: 10.1158/1538-7445.AM2019-3168 Retrieved from the Internet: URL:https://aacrjournals.org/cancerres/article/79/13_Supplement/3168/635006/Abstract-3168-Methods-for-assessment-of-the>* the whole document.

European Patent Office Search Report on EP application 20782135.6 dated Nov. 22, 2022 (16 pages).

Extended European Search Report issued in connection with EP Appl. Ser. No. 20770898.3 dated Oct. 17, 2022.

Le et al: "CD73 inhibition enhances the effect of anti-PD-1 therapy on KRAS-mutated pancreatic cancer model", Cancer Immunology Research Jul. 2014; AACR Special Conference on Tumor Immunology and Immunotherapy, Nov. 17, 2019 to Nov. 20, 2019 , Boston, MA, American Association for Cancer Research, US, [Online] vol. 8, No. 3 Suppl, Mar. 1, 2020 (Mar. 1, 2020), XP009539687, ISSN: 2326-607 4. Retrieved from the Internet: URL:https://aacrjournals.org/cancerimmunolres/article/8/3_ Supplement/ A46/ 469735/ Abs.

Pedraza-Farina Laura G: "Mechanisms of Oncogenic Cooperation in Cancer Initiation and Metastasis", Yale Journal of Biology and Medicine, Jan. 1, 2006 (Jan. 1, 2006), pp. 95-103, XP055967921, Retrieved from the Internet: URL:https://www.ncbi.nlm.nih.gov/pmc/articles/PMC1994802/pdf/ yjbm_79_3-4_095.pdf [retrieved on Oct. 4, 2022].

Roberto Leone et al: "Targeting adenosine 1,3-6, for cancer immunotherapy", 10-12, Journal for Immunotherapy of Cancer, 15,16, Biomed Central Ltd, London, UK, vol. 6, No. 1, Jun. 18, 2018 (Jun. 18, 2018), pp. 1-9, XP021257599, DOI: 10.1186/S40425-018-0360-8 p. 5; table 1.

Young Arabella et al: "Targeting Adenosine in BRAF-Mutant Melanoma Reduces Tumor Growth and Metastasis", Cancer research, vol. 77, No. 17, Sep. 1, 2017 (Sep. 1, 2017), pp. 4684-4696, XP055798544, 2019 San Antonio Breast Cancer Symposium, San Antonio, Texas ISSN: 0008-5472, Doi: 10.1158/0008-5472.CAN-17-0393 Retrieved from the Internet: URL:https://cancerres.aacrjournals.org/content/canres/77/17/4684.full.pdf.

U.S. Appl. No. 17/193,473, filed Mar. 5, 2021, Lawson et al.
U.S. Appl. No. 17/346,918, filed Jun. 14, 2021, Beatty et al.
U.S. Appl. No. 17/507,921, filed Oct. 22, 2021, Beatty et al.
International Search Report and Written Opinion dated Oct. 14, 2021 in PCT/US2020/025242, 11 pages.
International Search Report and Written Opinion dated Sep. 23, 2021 in PCT/US2020/022028, 8 pages.
Mittal et al., "Antimetastatic Effects of Blocking PD-1 and the Adenosine A2A Receptor," Cancer Research, Jul. 1, 2014, 74(14):3652-3658.
Stagg et al., "Anti-CD73 antibody therapy inhibits breast tumor growth and metastasis," PNAS, Jan. 26, 2010, 107(4):1547-1552.
Stagg et al., "Extracellular adenosine triphosphate and adenosine in cancer," Oncogene, Jul. 26, 2010, 29(39):5346-5358.
Azambuja et al., CD73 Downregulation Decreases In Vitro and In Vivo Glioblastoma Growth. Molecular Neurobiology (2019) 56:3260-3279, XP036763020.
Cushman et al., Gene expression markers of efficacy and resistance to cetuximab treatment in metastatic colorectal cancer: results from CALGB 80203 (Alliance), Clin Cancer Res. 2015; 21(5): 1078-1086.
DiRenzo et al, Development of biomarkers to assess adenosine generation & activity in support of clinical trials conducted with the adenosine receptor antagonist AB928, Journal for Immuno Therapy of Cancer 2018, 6(Suppl 1): P35, p. 18.
DiRenzo et al., Abstract 3168: Methods for assessment of the "adenosine fingerprint" in clinical trials of AB928, Cancer Res (2019) 79 (13_Supplement): 3168.
Gao et al., CD73 promotes proliferation and migration of human cervical cancer cells independent of its enzyme activity, BMC Cancer (2017) 17:135, XP093203406.
Häusler et al., Ectonucleotidases CD39 and CD73 on OvCA cells are potent adenosine-generating enzymes responsible for adenosine receptor 2A-dependent suppression of T cell function and NK cell cytotoxicity. Cancer Immunol Immunother 2011, 60:1405-1418, XP019954940.
International Preliminary Report on Patentability for International Application No. PCT/US2020/025242 dated Sep. 28, 2021. 9 pages.
Linden et al., Purine Release, Metabolism, and Signaling in the Inflammatory Response, Annual Review of Immunology 2019, vol. 37, pp. 325-347.
Rao et al., Tumour-derived alkaline phosphatase regulates tumour growth, epithelial plasticity and disease-free survival in metastatic prostate cancer, British Journal of Cancer (2017), 116, pp. 227-236.
Tsuji et al., Potential responders to FOLFOX therapy for colorectal cancer by Random Forests analysis, British Journal of Cancer (2012) 106, 126-132.
Turcotte et al., CD73 Is Associated with Poor Prognosis in High-Grade Serous Ovarian Cancer, Cancer Res 2015; 75(21); 4494-4503.
Wu et al., High expression of CD73 as a poor prognostic biomarker in human colorectal cancer, Journal of Surgical Oncology 2012; 106:130-137.
Yu et al., Extracellular 5'-nucleotidase (CD73) promotes human breast cancer cells growth through AKT/GSK-3B/B-catenin/cyclinD1 signaling pathway, International Journal of Cancer 2018, vol. 142, No. 5, pp. 959-967, XP093203410.
Zhou et al., The distinct role of CD73 in the progression of pancreatic cancer, Journal of Molecular Medicine (2019) 97:803-815.
Morello et al., "Soluble CD73 as biomarker in patients with metastatic melanoma patients treated with nivolumab," J. Transl. Med., Dec. 4, 2017, 15:244, 1-9.
Liu et al., Ovarian cancer stem-like cells with induced translineage-differentiation capacity and are suppressed by alkaline phosphatase inhibitor, Oncotarget 2013, vol. 4, No. 12, p. 2366-2382.
OVCAR-3, Cellosaurus, [date of retrieval: Apr. 5, 2024], cellosaurus.org/CVCL_0465.txt, 8 pages.
SK-OV-3, Cellosaurus, [date of retrieval: Apr. 5, 2024], cellosaurus.org/CVCL_0532.txt, 8 pages.

(56) References Cited

OTHER PUBLICATIONS

Wainberg et al., ARC-8: Phase 1/1b Randomized Study of Quemliclustat + Gemcitabine/Nab-Paclitaxel ± Zimberelimab in Patients With Treatment-Naive Metastatic Pancreatic Adenocarcinoma, Jan. 2024.

Zhao et al., Overexpression of CD73 in pancreatic ductal adenocarcinoma is associated with immunosuppressive tumor microenvironment and poor survival, Pancreatology 2021, 21(5): 942-949.

\* cited by examiner

TREATMENT OF CANCER UTILIZING AN IDENTIFIED ADENOSINE FINGERPRINT

CROSS-REFERENCES TO RELATED APPLICATIONS

This application is the U.S. National Stage of PCT/US2020/025242, filed Mar. 27, 2020, which claims the benefit of priority to U.S. Provisional Application No. 62/826,728, filed on Mar. 29, 2019, the contents of which are herein incorporated by reference for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BRIEF SUMMARY OF THE INVENTION

In some aspects, provided herein are methods of treating a cancer in a subject having an established adenosine fingerprint comprising administering to the subject a therapeutic agent targeting the extracellular production of adenosine and/or antagonizing the activation by adenosine of one of its receptors,
wherein the cancer in the subject has at least one of the features selected from the group consisting of
  (i) an increase in the concentration of one or more adenosine machinery proteins in blood from the subject, wherein the increase is relative to typical concentrations of the one or more adenosine machinery proteins in blood from subjects with the same type of cancer;
  (ii) an increase in the activity of CD73 or TNAP in blood from the subject as determined by an AMP hydrolysis assay, wherein the increase is relative to typical AMP hydrolysis activity of CD73 and/or TNAP in blood from subjects with the same type of cancer;
  (iii) a biopsy from the cancer of the subject that exhibits an increase in the amount of one or more adenosine machinery proteins as determined by immunostaining for one or more adenosine machinery proteins, wherein the increase is relative to typical amounts of the one or more adenosine machinery proteins in a biopsy from subjects with the same type of cancer; and
  (iv) a biopsy from the cancer of the subject that exhibits upregulation of one or more adenosine machinery proteins as determined by mRNA levels, wherein the upregulation is relative to typical amounts of the one or more adenosine machinery proteins in a biopsy from subjects with the same type of cancer.

In some aspects provided herein are kits and methods for detecting soluble CD73 concentrations in blood, and determining the CD73 mediated and/or TNAP mediated adenosine monophosphate (AMP) hydrolytic activity in a sample.

Other objects, features, and advantages of the present invention will be apparent to one of skill in the art from the following detailed description and figures.

DETAILED DESCRIPTION OF THE INVENTION

I. General

Figure 1:
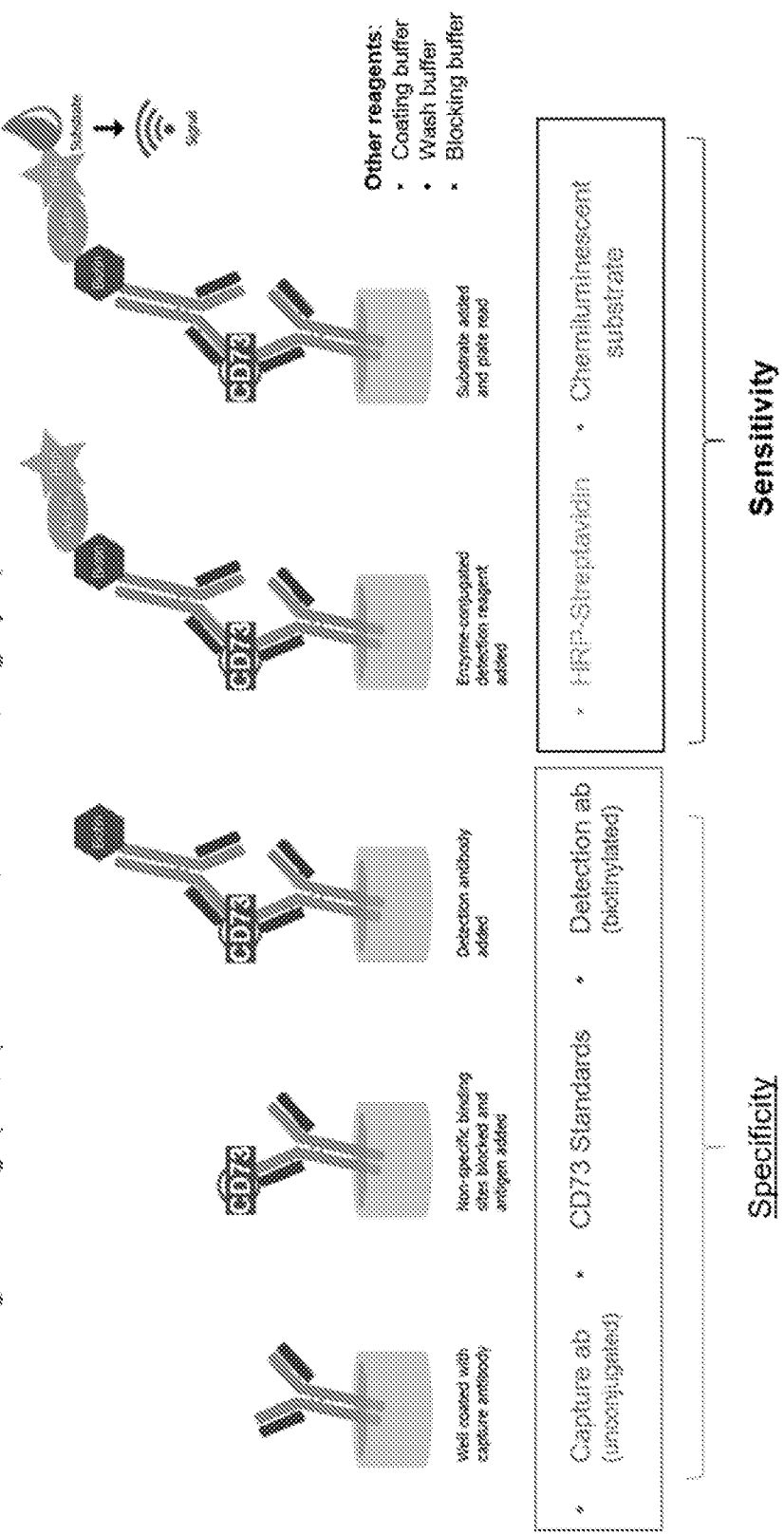
FIG. 1 shows a schematic summarizing the principles of the CD73 ELISA assay.

The present disclosure is drawn to the discovery that assessing and determining the adenosine fingerprint of a cancer in a subject provides methods for more effectively treating cancer. In particular, determining the adenosine fingerprint of a cancer provides a means for identifying subjects that will have a more favorable response to particular therapeutic regimens.

II. Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of $-(CH_2)_n-$, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups, often referred to as $X^1$ or $X^2$ groups in the present application, can be substituted or unsubstituted. When a group comprising $X^1$ or $X^2$ is optionally substituted, it is understood that the optional substitutions may be on the alkylene portion of the moiety.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. In some embodiments, the cycloalkyl compounds of the present disclosure are monocyclic $C_{3-6}$ cycloalkyl moieties.

The term "heterocycloalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycylic ring system. Non limiting examples of cyclohetroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A cycloheteroalkyl group can be attached to the remainder of the molecule through a ring carbon or a heteroatom.

As used herein, a wavy line, "〜", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O) NH—" is meant to include a linkage in either orientation: —C(O)NH— or —NHC(O)—, and similarly, "—O—$CH_2CH_2$—" is meant to include both —O—$CH_2CH_2$— and —$CH_2CH_2$—O—.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below.

Optional substituents for the alkyl radicals (including those groups often referred to as alkylene, alkenyl, and alkynyl) can be a variety of groups selected from:
halogen, —OR', —NR'R", —SR', —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN (cyano), —NO$_2$, aryl, aryloxy, oxo, cycloalkyl and heterocycloalkyl in a number ranging from zero to (2 m'+1), where m' is the total number of carbon atoms in such radical. R', R" and R'" each independently refer to hydrogen, unsubstituted $C_{1-8}$ alkyl, unsubstituted aryl, aryl substituted with 1-3 halogens, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Optional substituents for the cycloalkyl and heterocycloalkyl radicals can be a variety of groups selected from: alkyl optionally substituted with C(O)OR', halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN (cyano), —NO$_2$, aryl, aryloxy and oxo. R', R" and R'" each independently refer to hydrogen, unsubstituted $C_{1-8}$ alkyl, unsubstituted aryl, aryl substituted with 1-3 halogens, $C_{1-8}$ alkoxy or $C_{1-8}$ thioalkoxy groups, or unsubstituted aryl-$C_{1-4}$ alkyl groups.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{1-8}$haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-6 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CR$^f$R$^g$)$_r$—B—, wherein A and B are independently —CH$_2$—, —O—, —NH—, —S—, —S(O)—, —S(O)$_2$—, —S(O)$_2$NR'— or a single bond, r is an integer of from 1 to 3, and R$^f$ and R$^g$ are each independently H of halogen. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention. In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are described in more detail elsewhere herein.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of A2aR/A2bR (or another inhibitor or antagonist described herein) or a pharmaceutical composition comprising same to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of A2aR/A2bR or another inhibitor or antagonist described herein) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an A2aR/A2bR inhibitor or another inhibitor or antagonist described herein) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an A2aR/A2bR inhibitor (or, e.g., another inhibitor or antagonist described herein) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of an adenosine related protein described herein, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The term "adenosine machinery protein" or "adenosine machinery mRNA" or "adenosine machinery gene" refers to proteins, mRNA, or the encoding DNA, respectively, that are involved with the extracellular production of adenosine or involved in adenosine mediated signalling pathways. Exemplary proteins and the corresponding mRNA include, but are not limited to, adenosine A2a receptor (A2aR), adenosine A2b receptor (A2bR), adenosine A1 receptor (A1R), CD26, adenosine deaminase (ADA), tissue-nonspecific alkaline phosphatase (TNAP), CD73, ectonucleotide pyrophosphatase/phosphodiesterase 1 (ENPP1), CD38, and/or CD39.

The term "agent targeting the extracellular production of adenosine" refers to modulators of one or more proteins involved in the extracellular production of adenosine. Exemplary modulators include small molecule compounds, antibodies, and interfering RNA. Proteins involved in the extracellular production of adenosine include, but are not limited to tissue-nonspecific alkaline phosphatase (TNAP), CD73, ectonucleotide pyrophosphatase/phosphodiesterase 1 (ENPP1), CD38, and/or CD39. Thus, modulators known to target these proteins are relevant to the current disclosure.

The term "agent antagonizing the activation by adenosine of one of its receptors" refers to antagonists that reduce or fully prevent adenosine from binding with an adenosine receptor protein, often an integral membrane protein. Protein receptors that are activated by adenosine include, but are not limited to, adenosine A1 receptor (A1R), adenosine A2a receptor (A2aR) and/or adenosine A2b receptor (A2bR). Thus, antagonists known to target these receptors are relevant to the current disclosure.

III. Detailed Description of Embodiments

Disclosed herein are methods of establishing the adenosine fingerprint of a subject's cancer as a means for identifying subjects that will have a more favorable response to particular therapeutic regimens. Establishing the adenosine fingerprint in a subject is further described herein, but generally includes determining one or more of the following: the expression level of one or more adenosine machinery proteins in the subject's blood, the expression level of one or more adenosine machinery proteins (or mRNA levels) from a biopsy of the subject's tumor, the activity of particular adenosine machinery proteins in a subject's blood or tumor.

As such, also provided herein are methods of treating a cancer in a subject having an established adenosine fingerprint comprising administering to the subject a therapeutic agent targeting the extracellular production of adenosine and/or antagonizing the activation by adenosine of one of its receptors, wherein the cancer in the subject has at least one of the features selected from the group consisting of
(i) an increase in the concentration of one or more adenosine machinery proteins in blood from the subject, wherein the increase is relative to typical concentrations of the one or more adenosine machinery proteins in blood from subjects with the same type of cancer;
(ii) an increase in the activity of CD73 or TNAP in blood from the subject as determined by an AMP hydrolysis assay, wherein the increase is relative to typical AMP hydrolysis activity of CD73 and/or TNAP in blood from subjects with the same type of cancer;
(iii) a biopsy from the cancer of the subject that exhibits an increase in the amount of one or more adenosine machinery proteins as determined by immunostaining for one or more adenosine machinery proteins, wherein the increase is relative to typical amounts of the one or more adenosine machinery proteins in a biopsy from subjects with the same type of cancer; and
(iv) a biopsy from the cancer of the subject that exhibits upregulation of one or more adenosine machinery proteins as determined by mRNA levels, wherein the upregulation is relative to typical amounts of the one or more adenosine machinery proteins in a biopsy from subjects with the same type of cancer.

Adenosine Machinery Proteins

Extracellular adenosine in the tumor microenvironment has been shown to have immunosuppressive effects in various tumor models. Thus, the proteins involved in the production of extracellular adenosine and/or adenosine signaling (adenosine machinery proteins) are possible candidates for blocking, reducing, or inhibiting the immunosuppressive effects of adenosine. Adenosine machinery proteins include, but are not limited to, adenosine A2a receptor (A2aR), adenosine A2b receptor (A2bR), adenosine A1 receptor (A1R), CD26, Adenosine deaminase (ADA), tissue-nonspecific alkaline phosphatase (TNAP), CD73, ecto-nucleotide pyrophosphatase/phosphodiesterase 1 (ENPP1), CD38, and/or CD39.

Diagnostic tests that inform medical personnel about the expression level and/or activity level of adenosine machinery proteins provides a means for identifying subjects that will have a more favorable response to particular therapeutic regimens. As described below, assessing a cancer's adenosine fingerprint provides valuable information on the adenosine machinery proteins.

Adenosine Fingerprint of a Cancer

The adenosine fingerprint of a cancer can be used to inform decisions to identify and select suitable therapies for subjects with cancer. The adenosine fingerprint can include assessing the expression level and/or activity or one or more adenosine machinery proteins. The expression level can be the amount of mRNA in a cancer sample, the amount of expressed protein in the cancer sample, the amount of protein expressed in the blood of a subject with the cancer, or a combination of each of these assessments. Assessing the activity generally employs enzymatic assays using a sample of blood or a sample from the cancer that assesses the catalytic activity of an adenosine machinery protein.

Assessing the blood concentration of adenosine machinery proteins. Determining the blood concentration of one or more adenosine machinery proteins provides information on the quantity of relevant proteins expressed in a subject with the cancer. There are a number of known methods for determining the concentration of an analyte in a blood sample. One such example is a sandwich ELISA assay. Example 1 provides a description of determining the amount of soluble CD73 in a subject's blood sample. A number of other similar or related methods can be used to determine the concentration of one or more additional adenosine machinery proteins.

In some embodiments, when assessing the adenosine fingerprint of a subject, an increase in the concentration of one or more adenosine machinery proteins is considered relevant. The increase is determined relative to typical concentrations of one or more adenosine machinery proteins in blood from subjects with the same type of cancer. In some embodiments, typical concentrations of a given adenosine machinery protein is a threshold value in the blood from subjects with the same type of cancer. In some embodiments, typical concentrations of a given adenosine machinery protein is the average concentration of one or more adenosine machinery proteins in blood from subjects with the same type of cancer. In some embodiments, the increase is relative to the concentration of one or more adenosine machinery proteins in the subject prior to diagnosis with the cancer.

In some embodiments, when assessing the adenosine fingerprint, the soluble CD73 concentration is considered a relevant threshold value. For example, in some embodiments, a soluble CD73 concentration of about 1 ng/mL in blood from the subject is considered relevant threshold value. In some embodiments, the threshold value is 3 ng/mL. In some embodiments, the threshold value is 8 ng/mL.

In some embodiments, elevated levels of adenosine machinery proteins in the context of determining an adenosine fingerprint, are determined by measuring a relative increases over a reference standard level. Reference standard levels can be threshold values or the average level of a given protein in subjects with the same type of cancer. For example, in some embodiments, the soluble CD73 concentration in blood from a subject with a cancer is considered relevant when there is at least a 1% increase over a reference standard level. In some embodiments, an increase of about 2, 3, 4, 5, 10, 15, 20, 25, or more percent over a reference standard level is considered relevant.

Assessing the enzymatic activity of adenosine machinery proteins using an AMP hydrolysis assay. Determining the enzymatic activity of one or more adenosine machinery proteins provides information on the activity of relevant proteins expressed in a subject with the cancer. These determinations can be made from blood samples taken from a subject with the cancer. There are a number of known methods for determining the activity of protein in a blood sample. One particularly relevant assay for measuring the activity of CD73 or TNAP in the current disclosure is the AMP-Glo hydrolysis assay described in Example 2 of the current application.

The amount of AMP hydrolysis mediated by CD73, TNAP, or another protein can be reported in a number of different ways. In some embodiments, the CD73 and/or TNAP mediated hydrolysis in a sample is reported as the percent of the total AMP hydrolysis activity in the sample. In the context of determining the adenosine fingerprint, results from the AMP hydrolysis assay can indicate that treatment with one or more agents targeting the extracellular production of adenosine or agents antagonizing the activation by adenosine of one of its receptors are appropriate.

In some embodiments, when assessing the adenosine fingerprint of a subject via an AMP hydrolysis assay, an increase in the activity of CD73 and/or TNAP is considered relevant. The increase is determined relative to typical AMP hydrolysis activity of CD73 and/or TNAP in blood from subjects with the same type of cancer. In some embodiments, typical AMP hydrolysis activity of CD73 and/or TNAP is a threshold value in subjects with the same type of cancer. In some embodiments, typical AMP hydrolysis activity of CD73 and/or TNAP is the average AMP hydrolysis activity of one or more adenosine machinery proteins in blood from subjects with the same type of cancer. In some embodiments, the increase is relative to the AMP hydrolysis activity of CD73 and/or TNAP in the blood of the subject prior to diagnosis with the cancer.

In some embodiments, when assessing the adenosine fingerprint of a subject via an AMP-Glo hydrolysis assay, a threshold level of AMP mediated hydrolysis by an adenosine machinery protein is considered relevant. In some embodiments, such results include values where at least 10% of the total AMP hydrolysis activity in the blood of the subject is mediated by CD73 or TNAP; where at least 20% of the total AMP hydrolysis activity in the blood of the subject is mediated by CD73 or TNAP; or where at least 50% of the total AMP hydrolysis activity in the blood of the subject is mediated by CD73 or TNAP.

In some embodiments, assessing the enzymatic activity of adenosine machinery proteins is done using an isotopic AMP hydrolysis assay described in Example 7 of the current application.

In some embodiments, when assessing the adenosine fingerprint of a subject via an isotopic AMP hydrolysis assay, an increase in the isotopic AMP hydrolysis activity of CD73 and/or TNAP is considered relevant. The increase is determined relative to typical isotopic AMP hydrolysis activity of CD73 and/or TNAP in blood from subjects with the same type of cancer. In some embodiments, typical isotopic AMP hydrolysis activity of CD73 and/or TNAP is an increase above a threshold value in subjects with the same type of cancer. In some embodiments, typical isotopic AMP hydrolysis activity of CD73 and/or TNAP is the average isotopic AMP hydrolysis activity of one or more adenosine machinery proteins in blood from subjects with the same type of cancer. In some embodiments, the increase is relative to the isotopic AMP hydrolysis activity of CD73 and/or TNAP in the blood of the subject prior to diagnosis with the cancer.

In some embodiments, when assessing the adenosine fingerprint of a subject via an isotopic AMP hydrolysis assay, an threshold level of AMP mediated hydrolysis by an adenosine machinery protein is considered relevant. In some embodiments, such results include values where at least 10% of the total AMP hydrolysis activity in the blood of the subject is mediated by CD73 or TNAP; where at least 20% of the total AMP hydrolysis activity in the blood of the subject is mediated by CD73 or TNAP; or where at least 50% of the total AMP hydrolysis activity in the blood of the subject is mediated by CD73 or TNAP.

Assessing the expression level of adenosine machinery proteins in the tumor using immunostaining. Immunostaining is a well-established technique for identifying the presence of particular proteins and for quantitating relative amounts of said proteins. There are a number of methods available for labeling said proteins for visualization and quantitation. Typically, immunostaining includes obtaining a biopsy of the tumor from a subject with the cancer and applying a labeled antibody that binds to the target of interest. Exemplary methods for determining the amount of CD73 and TNAP are described in Example 3. A person of skill in the art will recognize that further adenosine machinery proteins can be assessed using similar techniques to those described in Example 3 or based on known methods in the art.

In some embodiments, when assessing the adenosine fingerprint of a subject via immunostaining, an increase in an adenosine machinery protein is considered relevant. The increase is determined relative to typical amounts of such adenosine machinery protein in a biopsy from subjects with the same type of cancer. In some embodiments, typical amounts of a given adenosine machinery protein is a threshold value in a biopsy from subjects with the same type of cancer. In some embodiments, typical amounts of a given adenosine machinery protein is the average amount of such adenosine machinery proteins in a biopsy from subjects with the same type of cancer. In some embodiments, the increase is relative to the amount of adenosine machinery protein in the same tissue of the subject prior to diagnosis with the cancer.

In some embodiments, when assessing the adenosine fingerprint of a subject via immunostaining, the percent staining area of the analyte of interest is considered a relevant threshold value. For example, in some embodiments, a staining area of 1% is considered a relevant threshold value. In some embodiments, a staining area of 7, 10, 20% or more is considered relevant threshold value.

Assessing the adenosine machinery protein by measuring mRNA levels. A number of methods that identify and quantitate relative mRNA levels in a biological sample are known in the art, each of which are appropriate for assessing the adenosine machinery mRNA levels. As contemplated herein, in some embodiments, a method for measuring mRNA levels is performed from a biopsy of the tumor from a subject. Exemplary methods for determine mRNA levels of adenosine machinery proteins are described in Example 4.

In some embodiments, when assessing the adenosine fingerprint of a subject via the measurement of mRNA levels, upregulation in an adenosine machinery mRNA is considered relevant. Upregulation is determined relative to typical amounts of the adenosine machinery mRNA in a biopsy from subjects with the same type of cancer. In some embodiments, typical amounts of a given adenosine machinery mRNA is a threshold value in a biopsy from subjects with the same type of cancer. In some embodiments, typical amounts of a given adenosine machinery mRNA is the average amount of such adenosine machinery mRNA in biopsies from subjects with the same type of cancer. In some embodiments, the increase is relative to the amount of adenosine machinery mRNA in the same tissue of the subject prior to diagnosis with the cancer.

Thus, in some embodiments, the disclosure here provides methods for treating a cancer in a subject having an established adenosine fingerprint comprising administering to the subject a therapeutic agent selected from the group consisting of an adenosine A2a receptor (A2aR) and/or adenosine A2b receptor (A2bR) antagonist and a CD73 inhibitor,
wherein the subject is administered a CD73 inhibitor when the cancer in the subject has at least one of the features selected from the group consisting of
  (i) an increase in the concentration of soluble CD73 in blood from the subject, wherein the increase is relative to typical concentrations of CD73 in blood from subjects with the same type of cancer;
  (ii) an increase in the activity of CD73 in blood from the subject as determined by an AMP hydrolysis assay, wherein the increase is relative to typical AMP hydrolysis activity of CD73 in blood from subjects with the same type of cancer;
  (iii) a biopsy from the cancer of the subject that exhibits an increase in the amount of CD73 as determined by immunostaining for CD73, wherein the increase is relative to typical amounts of CD73 in a biopsy from subjects with the same type of cancer; and
  (iv) a biopsy from the cancer of the subject that exhibits upregulation of CD73 as determined by mRNA levels, wherein the upregulation is relative to typical amounts of CD73 in a biopsy from subjects with the same type of cancer;
wherein the subject is administered adenosine A2a receptor (A2aR) or adenosine A2b receptor (A2bR) antagonist when the cancer in the subject has at least one of the features selected from the group consisting of
  (a) an increase in the concentration of TNAP in blood from the subject, wherein the increase is relative to typical concentrations of TNAP in blood from subjects with the same type of cancer;
  (b) an increase in the activity of TNAP in blood from the subject as determined by an AMP hydrolysis assay, wherein the increase is relative to typical AMP hydrolysis activity of TNAP in blood from subjects with the same type of cancer;
  (c) a biopsy from the cancer of the subject that exhibits an increase in the amount of TNAP as determined by immunostaining for TNAP, wherein the increase is relative to typical amounts of TNAP in a biopsy from subjects with the same type of cancer;
  (d) a biopsy from the cancer of the subject that exhibits upregulation of TNAP as determined by mRNA levels, wherein the upregulation is relative to typical amounts of TNAP in a biopsy from subjects with the same type of cancer.

In some embodiments, the subject is administered a CD73 inhibitor when the cancer in the subject has at least two, three, or four of the features selected from the group consisting of (i) through (iv); or the subject is administered adenosine A2a receptor (A2aR) or adenosine A2b receptor (A2bR) antagonist when the cancer in the subject has at least two, three, or four of the features selected from the group consisting of (a) through (d).

In some embodiments, the subject is administered only an adenosine A2a receptor (A2aR) or adenosine A2b receptor (A2bR) antagonist when the cancer in the subject exhibits at least one, two, three, or four of the features selected from each of (i) to (iv) and (a) to (d).

In some embodiments, the subject is administered both an adenosine A2a receptor (A2aR) and/or adenosine A2b receptor (A2bR) antagonist and a CD73 inhibitor when the cancer in the subject exhibits at least one, two, three, or four of the features selected from each of (i) to (iv) and (a) to (d).

The assessment of one or more of the features described herein aids in identifying subjects who will more favorably respond to selected therapeutic agents. These agents include agents targeting the extracellular production of adenosine as well as agents antagonizing the activation by adenosine of one of its receptors.

Agents Targeting the Extracellular Production of Adenosine

A number of proteins are known to be involved in the extracellular production of adenosine in the body. For example, a dominant pathway leading to the generation of extracellular adenosine is the sequential dephosphorylation of ATP by CD39, which hydrolyzes ATP to ADP and then AMP, and CD73, which hydrolyzes AMP to adenosine. TNAP also contributes to the production of adenosine from AMP. An alternative mechanism leading to the generation of extracellular adenosine is the hydrolysis of NAD+ to ADPR by CD38, and ADPR to AMP by ENPP1. ENPP1 may also hydrolyze NAD+ to produce AMP. Thus, proteins involved in the extracellular production of adenosine include, but are not limited to tissue-nonspecific alkaline phosphatase (TNAP), CD73, ectonucleotide pyrophosphatase/phosphodiesterase 1 (ENPP1), CD38, and/or CD39.

As contemplated herein, the present disclosure provides for methods of treating cancer in a subject having an established adenosine fingerprint using one or more agents that target the extracellular production of adenosine.

Tissue-nonspecific alkaline phosphatase (TNAP) inhibitors. Several TNAP inhibitors are known in the art. In some embodiments, the TNAP inhibitor useful in the described methods is an agent disclosed in WO/2013/126608, WO/2006/039480, or WO/2002/092020, the contents of each is hereby incorporated by reference for all purposes. In some embodiments, the TNAP inhibitor has the formula:

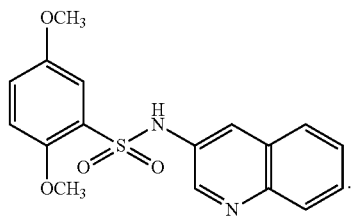 [SMILES: COc1ccc(OC)c(S(=O)(=O)Nc2cnc3ccccc3c2)c1]

CD73 Inhibitors. In some embodiments, the CD73 inhibitors useful in the described methods are compounds of Formula (i)

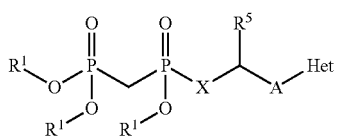
(i)

or a pharmaceutically acceptable salt, hydrate, or solvate thereof, wherein, each $R^1$ is independently selected from the group consisting of hydrogen, optionally substituted $C_1$-$C_6$ alkyl, optionally substituted aryl, and —C($R^2R^2$)—O—C(O)—OR$^3$, or two $R^1$ groups are optionally combined to form a 5- to 7-membered ring;

each $R^2$ is independently selected from the group consisting of H and optionally substituted $C_1$-$C_6$ alkyl;

each $R^3$ is independently selected from the group consisting of H, $C_1$-$C_6$ alkyl, and optionally substituted aryl;

$R^5$ is selected from the group consisting of H and optionally substituted $C_1$-$C_6$ alkyl;

X is selected from the group consisting of O, $CH_2$, and S;

A is selected from the group consisting of:

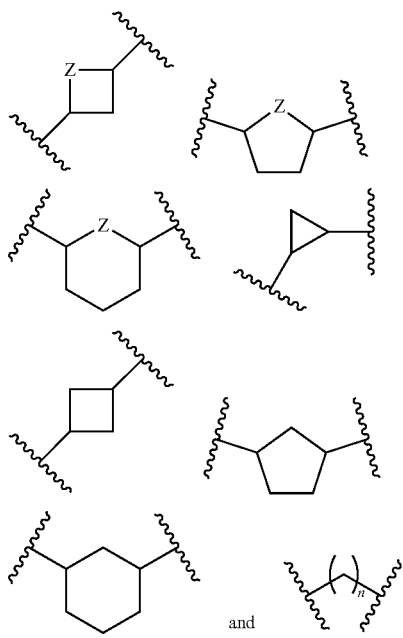

and each of which is optionally substituted with from 1 to 5 $R^6$ substituents, and wherein the subscript n is an integer from 0 to 3;

Z is selected from the group consisting of $CH_2$, $CHR^6$, $NR^6$, and O;

each $R^6$ is independently selected from the group consisting of H, $CH_3$, OH, CN, F, optionally substituted $C_1$-$C_6$ alkyl, and OC(O)—$C_1$-$C_6$ alkyl; and optionally two $R^6$ groups on adjacent ring vertices are joined together to form a 5- to 6-membered ring having at least one heteroatom as a ring vertex; and Het is selected from the group consisting of:

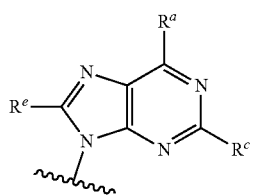
a1

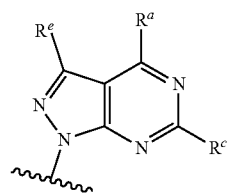
a2

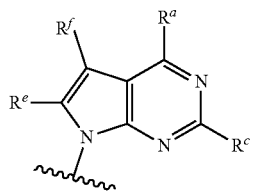
a3

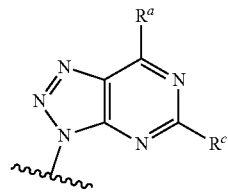
a4

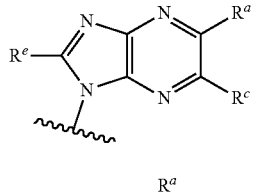
a5

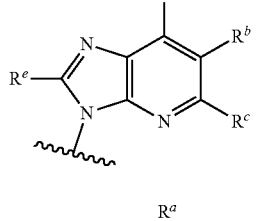
a6

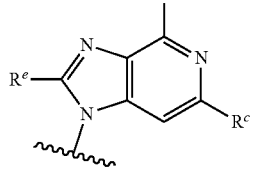
a7

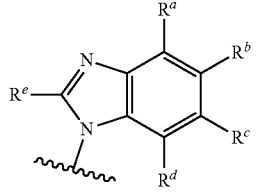
a8

-continued a9
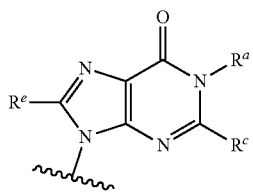

a10
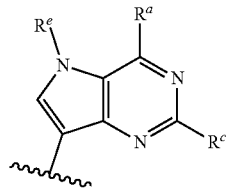

a11
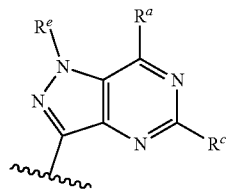

a12
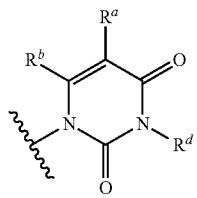

a13
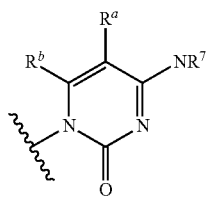

a14
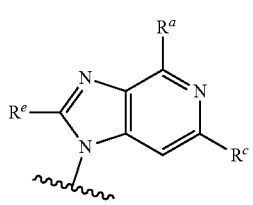

a15
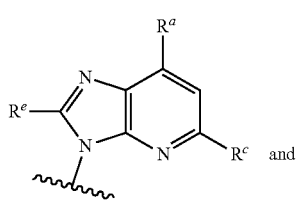

a16
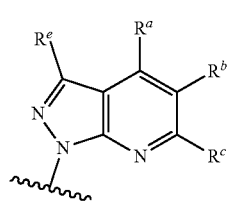

wherein the wavy line indicates the point of attachment to the remainder of the compound, and wherein:

$R^a$ is selected from the group consisting of H, $NH_2$, $NHR^7$, $NHC(O)R^7$, $NR^7R^7$, $R^7$, OH, $SR^7$ and $OR^7$;

$R^b$ is selected from the group consisting of H, halogen, $NH_2$, $NHR^7$, $NR^7R^7$, $R^7$, OH, and $OR^7$;

$R^c$ and $R^d$ are independently selected from the group consisting of H, halogen, haloalkyl, $NH_2$, $NHR^7$, $NR^7R^7$, $R^7$, OH, $OR^7$, $SR^7$, $SO_2R^7$, $-X^1-NH_2$, $-X^1-NHR^7$, $-X^1-NR^7R^7$, $-X^1-OH$, $-X^1-OR^7$, $-X^1-SR^7$ and $-X^1-SO_2R^7$;

$R^e$ and $R^f$ are independently selected from the group consisting of H, halogen, and optionally substituted $C_1$-$C_6$ alkyl;

each $X^1$ is $C_1$-$C_4$alkylene; and each $R^7$ is independently selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_7$ cycloalkyl, optionally substituted $C_3$-$C_7$ cycloalkyl$C_1$-$C_4$alkyl, optionally substituted 4-7 membered cycloheteroalkyl, optionally substituted 4-7 membered cycloheteroalkyl$C_1$-$C_4$alkyl, optionally substituted aryl, optionally substituted aryl$C_1$-$C_4$alkyl, optionally substituted aryl$C_2$-$C_4$alkenyl, optionally substituted aryl$C_2$-$C_4$alkynyl, optionally substituted heteroaryl, optionally substituted heteroaryl$C_1$-$C_4$alkyl, optionally substituted heteroaryl$C_1$-$C_4$alkenyl, optionally substituted heteroaryl$C_2$-$C_4$alkynyl, and optionally, two $R^7$ groups attached to a nitrogen atom are joined together to form a 4- to 7-membered heterocyclic ring, optionally fused to an aryl ring;

with the proviso that the compounds are other than those compounds wherein the combination of X, A, and Het results in

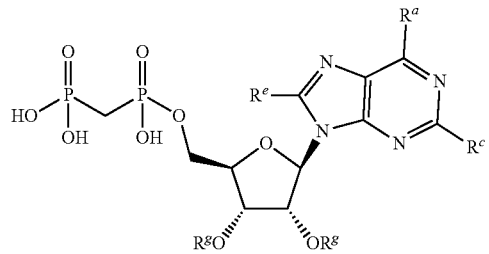

wherein $R^g$ is H or the two $R^g$ groups are combined to form an acetonide; and either (1) $R^c$ and $R^e$ are hydrogen and $R^a$ is —OEt, —OCH$_2$Ph, —SCH$_2$Ph, —NH$_2$, methylamino, ethylamino, dimethylamino, diethylamino, N-methyl-N-ethylamino, phenylamino, benzylamino, 2-phenylethylamino, N-benzyl-N-ethylamino, dibenzylamino, 4-aminobenzylamino, 4-chlorobenzylamino, 4-nitrobenzylamino, or 4-sulfamoylbenzylamino; or (2) $R^c$ is hydrogen, $R^a$ is —NH$_2$, and $R^e$ is bromo, chloro, aminomethyl, or thioethyl; or (3) $R^c$ is hydrogen, $R^a$ is benzylamino, and $R^e$ is bromo.

In some embodiments, the CD73 inhibitor is Compound A

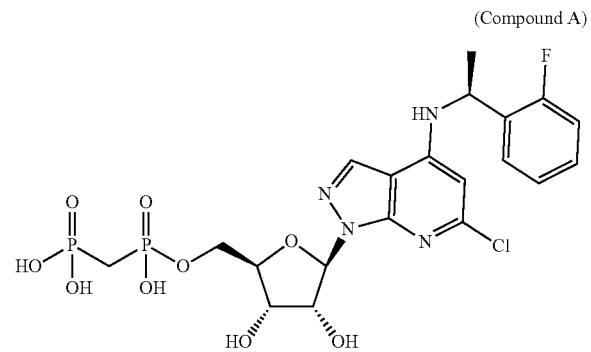 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

(Compound A)

or a pharmaceutically acceptable salt thereof.

In some embodiments, the CD73 inhibitor is Compound B

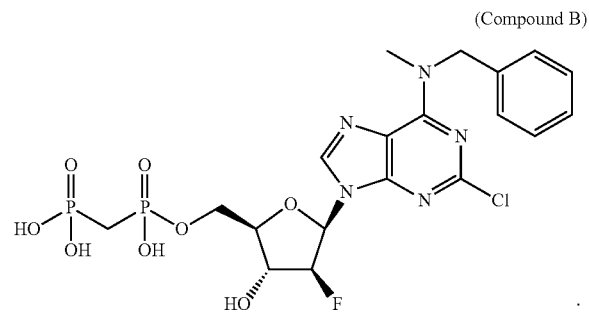 [SMILES: CN(Cc1ccccc1)c1nc(Cl)nc2c1ncn2[C@@H]1O[C@H](COP(=O)(O)CP(=O)(O)O)[C@@H](O)[C@@H]1F]

(Compound B)

or a pharmaceutically acceptable salt thereof.

In some embodiments, the CD73 inhibitor is Compound C

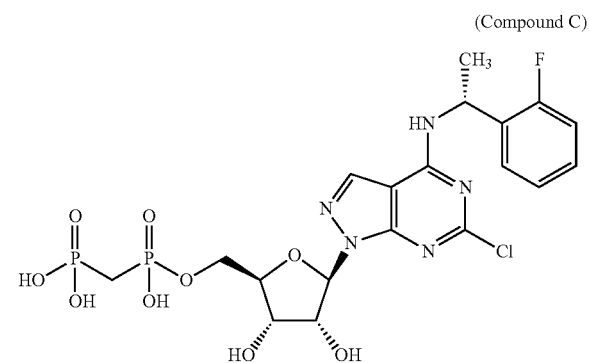 [SMILES: C[C@@H](Nc1nc(Cl)nc2c1cnn2[C@@H]1O[C@H](COP(=O)(O)CP(=O)(O)O)[C@@H](O)[C@H]1O)c1ccccc1F]

(Compound C)

or a pharmaceutically acceptable salt thereof.

In some embodiments, the CD73 inhibitor is a molecule described in US Pat. Pub. 2017/0267710 (see, U.S. application Ser. No. 15/400,748, filed on Jun. 6, 2017), the content of which is hereby incorporated by reference for all purposes.

In some embodiments, the CD73 inhibitor is an agent disclosed in WO2015/164573, WO2017/120508, WO2018/183635, WO2018/094148, WO2018/119284, WO2018/183635, WO2018/208727, WO2018/208980, WO2017/098421, WO2017/153952, the contents of each is hereby incorporated by reference for all purposes.

In some embodiments, the CD73 inhibitor is oleclumab (MEDI-9447), CPI-006, NZV930/SRF373, BMS-986179, or TJ4309.

Ectonucleotide pyrophosphatase/phosphodiesterase 1 (ENPP1) inhibitors. In some embodiments, the ectonucleotide pyrophosphatase/phosphodiesterase 1 (ENPP1) inhibitor useful in the described methods is MV-626.

In some embodiments, the ENPP1 inhibitor useful in the described methods is an agent disclosed in WO2019/023635, the content of which is hereby incorporated by reference for all purposes.

CD 38 Inhibitors. In some embodiments, the CD38 inhibitors useful in the described methods are daratumumab or isatuximab.

In some embodiments, the CD38 inhibitor is an agent disclosed in WO/2019/034753, US2018/0298106, WO2019/034752, the content of each is hereby incorporated by reference for all purposes.

CD 39 Inhibitors. CD39 is also known as ectonucleoside triphosphate diphosphohydrolase-1. In some embodiments, the CD39 inhibitor useful in the described methods is IPH5201, SRF617, or TTX-030.

In some embodiments, the CD39 inhibitor is an agent disclosed in WO2012/085132, WO2017/089334, WO2009/095478, WO2011/154453, and WO2018/224685, the content of each is hereby incorporated by reference for all purposes.

The present disclosure encompasses pharmaceutically acceptable salts, or derivatives of any of the above.

Agents Antagonizing the Activation by Adenosine of One of its Receptors

There are a number of receptors in the body that are activated by extracellular adenosine. That is, the binding of adenosine initiates an enzymatic activity and/or propagates a cellular signal. Activation by adenosine occurs via four G-coupled adenosine receptors: A1, A2a, A2b and A3. Adenosine largely signals through the A2a receptor (expressed primarily on T cells) and A2b receptor (expressed on myeloid cells), which when stimulated by adenosine, leads to impaired T-cell activation. While less understood, the A1 receptor has been reported to be involved in the pathogenesis of cancers such as breast, colon and gastric cancers, and the A3 receptor has been reported to be involved in colorectal and breast cancer. The over activation of one or more of these receptors by adenosine in a tumor microenvironment can lead to immunosuppressive effects. Thus, antagonists that can block or otherwise prevent the binding of adenosine to these receptors are useful in the treatment of cancers. Relevant receptors include, but are not limited to the adenosine A1 receptor (A1R), the adenosine A2a receptor (A2aR) and/or the adenosine A2b receptor, and the adenosine A3 receptor (A3R).

As contemplated herein, the present disclosure provides methods of treating a cancer in a subject having an established adenosine fingerprint using one or more agents that antagonizing the activation by adenosine of one of its receptors.

Adenosine A1 Receptor (A1R) Antagonists. In some embodiments, the A1R antagonist useful in the described methods is FK352, KW-3902 (Rolofylline), SLV320, BG9719 (CVT-124), or BG9928 (Adentri).

Adenosine A2a Receptor (A2aR) and/or Adenosine A2b Receptor (A2bR) Antagonists. In some embodiments, the adenosine A2a receptor (A2aR) and/or adenosine A2b receptor (A2bR) antagonists useful in the described methods are compounds of Formula (I)

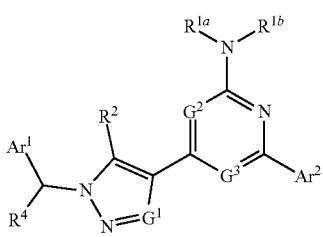

or a pharmaceutically acceptable salt, hydrate, or solvate thereof, wherein,
- $G^1$ is N or $CR^{3a}$;
- $G^2$ is N or $CR^{3b}$;
- $G^3$ is N or $CR^{3c}$;
- $R^{3a}$, $R^{3b}$, and $R^{3c}$ are each independently H or $C_{1-3}$ alkyl;
- $R^{1a}$ and $R^{1b}$ are each independently selected from the group consisting of
  - i) H
  - ii) $C_{1-8}$ alkyl optionally substituted with from 1-3 $R^5$ substituents,
  - iii) —$X^1$—O—$C_{1-8}$ alkyl optionally substituted with from 1-3 $R^5$ substituents,
  - iv) —C(O)—$R^6$,
  - v) Y optionally substituted with 1-3 $R^7$ substituents, and
  - vi) —$X^1$—Y optionally substituted with 1-3 $R^7$ substituents; or
  - vii) $R^{1a}$ and $R^{1b}$ together with the nitrogen to which they are attached form a 5-6 membered heterocycloalkyl ring optionally substituted with from 1-3 $R^8$ substituents, wherein the heterocycloalkyl has 0-2 additional heteroatom ring vertices selected from the group consisting of O, N, and S;
- each Y is $C_{3-8}$ cycloalkyl or 4 to 6-membered heterocycloalkyl having 1-3 heteroatom ring vertices selected from the group consisting of O, N, and S;
- $R^2$ and $R^4$ are each independently H or $C_{1-3}$ alkyl;
- $Ar^1$ is phenyl or a 5 to 6-membered heteroaryl, each of which is optionally substituted with 1-3 $R^9$;
- $Ar^2$ is phenyl or a 5 to 6-membered heteroaryl, each of which is optionally substituted with 1-3 $R^{10}$;
- wherein the 5 to 6-membered heteroaryl of $Ar^1$ and $Ar^2$ each independently have 1-3 heteroatom ring vertices selected from the group consisting of O, N, and S;
- each $X^1$ is $C_{1-6}$ alkylene;
- each $R^5$ is independently selected from the group consisting of hydroxyl, $C_{3-8}$ cycloalkyl, phenyl, —O-phenyl, —$C(O)OR^a$ and oxo;
- each $R^6$ is $C_{1-8}$ alkyl or Y, each of which is optionally substituted with 1-3 substituents selected from the group consisting of hydroxyl, —O-phenyl, phenyl, and —O—$C_{1-8}$ alkyl;
- each $R^7$ is independently selected from the group consisting of $C_{1-8}$ alkyl, hydroxyl, —O—$C_{1-8}$ alkyl, oxo, and $C(O)OR^a$;

- each $R^8$ is independently selected from the group consisting of $C_{1-8}$ alkyl, hydroxyl, and oxo;
- each $R^9$ is independently selected from the group consisting of $C_{1-8}$ alkyl, —O—$C_{1-8}$ alkyl, —$X^1$—O—$C_{1-8}$ alkyl, —O—$X^1$—O—$C_{1-8}$ alkyl, —$X^1$—O—$X^1$—O—$C_{1-8}$ alkyl, —$C(O)OR^a$, halogen, cyano, —$NR^bR^c$, Y, —$X^1$—$C_{3-8}$ cycloalkyl, and —$X^2$—Z, wherein $X^2$ is selected from the group consisting of $C_{1-6}$ alkylene, —$C_{1-6}$ alkylene-O—, —C(O)—, and —$S(O)_2$—, Z is 4 to 6-membered heterocycloalkyl having 1-3 heteroatom ring vertices selected from the group consisting of O, N, and S, and wherein each of said $R^9$ substituents is optionally substituted with 1-3 $R^{11}$;
- each $R^{10}$ is independently selected from the group consisting of $C_{1-8}$ alkyl, halo, cyano, —O—$C_{1-8}$ alkyl, —$X^1$—O—$C_{1-8}$ alkyl, —O—$X^1$—O—$C_{1-8}$ alkyl, —$S(O)_2$—$C_{1-6}$ alkyl, —$C(O)NR^dR^e$, and 4-6-membered heteroaryl having from 1-3 heteroatom ring vertices selected from the group consisting of O, N, and S, wherein each of said $R^{10}$ substituents is optionally substituted with 1-3 $R^{12}$, or two $R^{10}$ on adjacent ring vertices of $Ar^2$ are optionally combined to form a 5-membered heterocyclic ring optionally substituted with 1-2 halogens;
- each $R^{11}$ is independently selected from the group consisting of hydroxyl, halo, cyano, —$NR^dR^e$, —$C(O)OR^a$, phenyl, $C_{3-8}$ cycloalkyl, and $C_{1-4}$ alkyl optionally substituted with $C(O)OR^a$;
- each $R^{12}$ is independently selected from the group consisting of halo, cyano, hydroxy, —$C(O)OR^a$; and
- each $R^a$ is H or $C_{1-6}$ alkyl;
- each $R^b$ and $R^c$ are independently selected from the group consisting of H, $C_{1-8}$ alkyl, —$S(O)_2$-$C_{1-6}$ alkyl, —$C(O)OR^a$, and —$X^1$—$C(O)OR^a$;
- each $R^d$ and $R^e$ are independently selected from the group consisting of H, $C_{1-8}$ alkyl, —$S(O)_2$-$C_{1-6}$ alkyl; and provided that when $G^1$ and $G^2$ are each N, $G^3$ is CH, $R^2$ is $CH_3$, and $R^{1a}$ and $R^{1b}$ are each H, then $Ar^2$ is other than 2-thienyl, phenyl, 2-, 3- or 4-methoxyphenyl, 3- or 4-halophenyl, 2,4-dimethoxyphenyl, 2,4-dichlorophenyl or 2- or 4-methylphenyl.

In some embodiments, the adenosine A2a receptor (A2aR) or adenosine A2b receptor (A2bR) antagonist is Compound 1

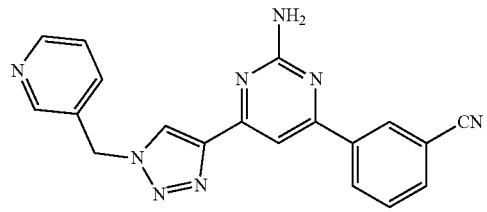

(Compound 1)

or a pharmaceutically acceptable salt thereof.

In some embodiments, the adenosine A2a receptor (A2aR) or adenosine A2b receptor (A2bR) antagonist is Compound 2

(Compound 2)

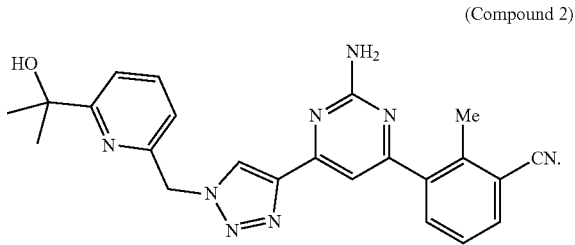 [SMILES: Cc1c(C#N)cccc1-c1cc(-c2cn(Cc3cccc(C(C)(C)O)n3)nn2)nc(N)n1]

or a pharmaceutically acceptable salt thereof.

In some embodiments, the adenosine A2a receptor (A2aR) or adenosine A2b receptor (A2bR) antagonist is Compound 3

(Compound 3)

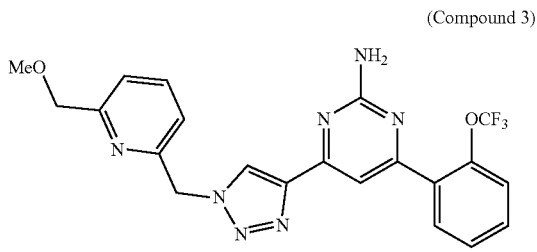 [SMILES: COCc1cccc(Cn2cc(-c3cc(-c4ccccc4OC(F)(F)F)nc(N)n3)nn2)n1]

or a pharmaceutically acceptable salt thereof.

In some embodiments, the adenosine A2a receptor (A2aR) and/or adenosine A2b receptor (A2bR) antagonist is a molecule described in US Pat. Pub. 2018/0215730 (see also U.S. application Ser. No. 15/875,106, filed Jun. 19, 2018, the content of which is hereby incorporated by reference for all purposes).

In some embodiments, the A2a receptor (A2aR) and/or adenosine A2b receptor (A2bR) antagonist is AZD4635, ciforadenant (CPI-444), NIR178, or PBF-1129.

Adenosine A3 Receptor (A3R) Antagonists. In some embodiments, the A3R antagonist useful in the described methods is a molecule described in WO2007/063539A1, US2003/0078232, the content of each are hereby incorporated by reference for all purposes.

Types of Cancer

A person of skill in the art will recognize that the treatment methods described herein are independent of tumor origin and rely on assessing the adenosine fingerprint of the tumor. As such, the present disclosure provides methods that are not limited to specific types of cancer. Thus, the present disclosure is useful in treating a number of different cancer types including, but not limited to, cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast (including triple negative breast cancer), muscle, connective tissue, lung (including small-cell lung carcinoma and non-small-cell lung carcinoma), adrenal gland, thyroid, kidney, or bone; glioblastoma, mesothelioma, renal cell carcinoma, gastric carcinoma, sarcoma (including Kaposi's sarcoma), choriocarcinoma, cutaneous basocellular carcinoma, and testicular seminoma.

In some embodiments of the present disclosure, the cancer is melanoma, colon cancer, pancreatic cancer, breast cancer, prostate cancer, lung cancer, leukemia, a brain tumor, lymphoma, sarcoma, ovarian cancer, head and neck cancer, cervical cancer or Kaposi's sarcoma.

In some embodiments of the present disclosure, the cancer is a cancer of the thyroid, adrenal gland, mesothelial lining, bile duct, pancreas, brain, kidney, esophagus, rectum, colon, stomach, head, neck, skin, testis, ovary, lung, endometrium, eye, prostate, breast, or liver; or is glioblastoma, mesothelioma or sarcoma.

In some embodiments of the present disclosure, the cancer is a cancer of the testis, ovary, lung, endometrium or adrenal gland.

In some embodiments of the present disclosure, the cancer is a cancer of the eye, prostate, breast, kidney, liver or lung.

In some embodiments, the present disclosure provides methods for treating a subject identified as having a specific type of cancer with an agent that targets the extracellular production of adenosine and/or an agent antagonizing the activation by adenosine of one of its receptors and at least one additional therapeutic, examples of which are set forth elsewhere herein.

Combination Therapy

The present disclosure contemplates the use of the therapeutic agents described herein alone or in combination with one or more active therapeutic agents. The additional active therapeutic agents can be small chemical molecules; macromolecules such as proteins, antibodies, peptibodies, peptides, DNA, RNA or fragments of such macromolecules; or cellular or gene therapies. In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the therapeutic agents described herein are administered or applied sequentially, e.g., where one agent is administered prior to one or more other agents. In other embodiments, the therapeutic agents described herein are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The agents that target the extracellular production of adenosine of the present disclosure and/or an agent antagonizing the activation by adenosine of one of its receptors may be used in combination with at least one other (active) agent in any manner appropriate under the circumstances. In one embodiment, treatment with the at least one active agent and at least one additional therapeutic agents described herein is maintained over a period of time. In another embodiment, treatment with the at least one active agent is reduced or discontinued (e.g., when the subject is stable), while treatment with a therapeutic agent described herein is maintained at a constant dosing regimen. In a further embodiment, treatment with the at least one active agent is reduced or discontinued (e.g., when the subject is stable), while treatment with a therapeutic agent described herein is reduced (e.g., lower dose, less frequent dosing or shorter treatment regimen). In yet another embodiment, treatment with the at least one active agent is reduced or discontinued (e.g., when the subject is stable), and treatment with a therapeutic agent described herein is increased (e.g., higher dose, more frequent dosing or longer treatment regimen). In yet another embodiment, treatment with the at least one active agent is maintained and treatment with the therapeutic agents described herein is reduced or discontinued (e.g., lower dose, less frequent dosing or shorter treatment regimen). In yet another embodiment, treatment with the at least one active agent and treatment with the therapeutic agents described herein are reduced or discontinued (e.g., lower dose, less frequent dosing or shorter treatment regimen).

The present disclosure provides methods for treating and/or preventing a cancer in a subject having an established adenosine fingerprint with an agent that targets the extracellular production of adenosine and/or an agent antagonizing the activation by adenosine of one of its receptors and at least one additional therapeutic or diagnostic agent. In some embodiments, the additional therapeutic is radiation, an immunomodulatory agent or chemotherapeutic agent. Suitable immunomodulatory agents that may be used in the present invention include CD4OL, B7, and B7RP1; activating monoclonal antibodies (mAbs) to stimulatory receptors, such as, anti-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, ILL IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); indoleamine 2,3-dioxygenase 1 (IDO1) inhibitors and immune-stimulatory oligonucleotides.

In certain embodiments, the present disclosure includes administration of the therapeutic agents described herein in combination with a signal transduction inhibitor (STI). As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in immunomodulation can also be used in combination with the therapeutic agents described herein for the suppression of tumor growth in cancer patients.

TMB is a useful tool for determining the total number of somatic mutations a subject has in their genome. This information can be used for the identification and selection of viable treatment options. For example, in some embodiments, the tumor mutation burden (TMB) in a subject is used to identify patients that should receive an additional chemotherapeutic agent. For example, in some embodiments, the methods provided herein include further administering to the subject a chemotherapeutic agent when the TMB is less than 2.0 as determined by whole exome sequencing (WES). In some embodiments, the subject is further administered a chemotherapeutic agent when the TMB is less than 2.5, 3, 3.5, 4, 4.5, 5, 6, 7, 8, 9, or 10.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; anthracyclines; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises a chemotherapy regimen that includes one or more chemotherapeutic agents. In certain embodiments, combination therapy comprises administration of a hormone or related hormonal agent.

Additional treatment modalities that may be used in combination with the therapeutic agents described herein include radiotherapy, a monoclonal antibody against a tumor antigen, a complex of a monoclonal antibody and toxin, a T-cell adjuvant, bone marrow transplant, or antigen presenting cells (e.g., dendritic cell therapy), including TLR agonists which are used to stimulate such antigen presenting cells.

In certain embodiments, the present disclosure contemplates the use of the therapeutic agents described herein in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

In certain embodiments, the present disclosure contemplates the use of the compounds described herein in combination with RNA interference-based therapies to silence gene expression. RNAi begins with the cleavage of longer double-stranded RNAs into small interfering RNAs (siRNAs). One strand of the siRNA is incorporated into a ribonucleoprotein complex known as the RNA-induced silencing complex (RISC), which is then used to identify mRNA molecules that are at least partially complementary to the incorporated siRNA strand. RISC can bind to or cleave the mRNA, both of which inhibits translation.

The present disclosure contemplates the use of the inhibitors of the therapeutic agents described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T-cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms.

In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor—ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively unregulated in various types of tumor cells, that are candidates for blockade include PD1 (programmed cell death protein 1); PD-L1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); TIGIT (T cell immunoreceptor with Ig and ITIM domains); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present disclosure contemplates the use of the therapeutic agents described herein in combination with inhibitors of the aforementioned immune-checkpoint receptors and ligands, as well as yet-to-be-described immune-checkpoint receptors and ligands. Certain modulators of immune checkpoints are currently available, including the PD1 and PD-L1 antibodies nivolumab (Bristol-Myers Squibb), pembrolizumab (Merck), cemiplimab (Sanofi and Regeneron), atezolizumab (Roche), durvalumab (AstraZeneca) and avelumab (Merck), whereas others are in development.

In some embodiments, the treatment methods described herein include the administration of a PD1 and PD-L1 inhibitor when a biopsy from the cancer of the subject indicates that the cancer is PD-L1 positive. Methods for determining PD-L1 status are known in the art and Example 6 of the current application references an FDA approved product for determining PD-L1 status. In some embodiments, a subject is considered to be PD-L1 positive when at least 1% of cells from the cancer express PD-L1. In some embodiments, a subject is considered to be PD-L1 positive when at least 10% of cells from the cancer express PD-L1.

In some embodiments, a subject is considered to be PD-L1 positive when at least 50% of cells from the cancer express PD-L1. Similar assays can be performed to determine the status of other immune checkpoints in a subject tumor.

In one aspect of the present invention, the therapeutic agents described herein are combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD4OL, OX-40, OX-40L, CD70, CD27L, CD30, CD3OL, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT13R, LIGHT, DcR3, HVEM, VEGI/TL1A, TRAMP/DR3, EDAR, EDA1, XEDAR, EDA2, TNFR1, Lymphotoxin a/TNF13, TNFR2, TNFa, LT13R, Lymphotoxin a 1132, FAS, FASL, RELT, DR6, TROY, NGFR.

In another aspect, the immuno-oncology agent is a cytokine that inhibits T cell activation (e.g., IL-6, IL-10, TGF-B, VEGF, and other immunosuppressive cytokines) or a cytokine that stimulates T cell activation, for stimulating an immune response.

In one aspect, T cell responses can be stimulated by a combination of the therapeutic agents described herein and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX4OL, GITR, GITRL, CD70, CD27, CD40, DR3 and CD2. Other agents that can be combined with the therapeutic agents described herein for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (W011/70024, W011/107553, W011/131407, W013/87699, W013/119716, W013/132044) or FPA-008 (W011/140249; W013169264; W014/036357).

In another aspect, the disclosed agents that target the proteins/receptors described herein can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), MEDI-0680 (AMP-514; W02012/145493), BGB-108, GB-226, PDR-001, mDX-400, SHR-1210, IBI-308, PF-06801591. The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, MPDL3280A (RG7446; W02010/077634), durvalumab (MEDI4736), atezolizumab, avelumab, BMS-936559 (W02007/005874), MSB0010718C (W02013/79174), KD-033, CA-327, CA-170, ALN-PDL, TSR-042, and STI-1014.

In another aspect, the immuno-oncology agent is a LAG-3 antagonist, such as an antagonistic LAG-3 antibody. Suitable LAG3 antibodies include, for example, BMS-986016 (W010/19570, W014/08218), or IMP-731 or IMP-321 (W008/132601, W009/44273).

In another aspect, the immuno-oncology agent is a CD137 (4-1BB) agonist, such as an agonistic CD137 antibody. Suitable CD137 antibodies include, for example, urelumab and PF-05082566 (W012/32433).

In another aspect, the immuno-oncology agent is a GITR agonist, such as an agonistic GITR antibody. Suitable GITR antibodies include, for example, BMS-986153, BMS-986156, TRX-518 (W006/105021, W009/009116) and MK-4166 (W011/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX4OL antagonist, such as an antagonistic OX40 antibody. Suitable OX4OL antagonists include, for example, RG-7888 (W006/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (W011/109400).

Dosing

The agents that target the extracellular production of adenosine and/or agents antagonizing the activation by adenosine of one of its receptors of the present disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of agents that target the therapeutic agents described herein may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the therapeutic agents described herein may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In additional to oral dosing, suitable routes of administration for certain agents described herein include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), and intraocular. Depot injections, which are generally administered subcutaneously or intramuscularly, may also be utilized to release the agents described herein over a defined period of time.

In certain embodiments, the dosage of the desired agents the therapeutic agents described herein is contained in a "unit dosage form". The phrase "unit dosage form" refers to physically discrete units, each unit containing a predetermined amount of the therapeutic agents described herein, either alone or in combination with one or more additional agents, sufficient to produce the desired effect. It will be appreciated that the parameters of a unit dosage form will depend on the particular agent and the effect to be achieved.

Kits & Detection Methods

The present disclosure also contemplates kits comprising the therapeutic agents described herein, and pharmaceutical compositions thereof. The kits are generally in the form of a physical structure housing various components, as described below, and may be utilized, for example, in practicing the methods described above.

A kit can include one or more of the compounds disclosed herein (provided in, e.g., a sterile container), which may be in the form of a pharmaceutical composition suitable for administration to a subject. The compounds described herein can be provided in a form that is ready for use (e.g., a tablet or capsule) or in a form requiring, for example, reconstitution or dilution (e.g., a powder) prior to administration. When the compounds described herein are in a form that needs to be reconstituted or diluted by a user, the kit may also include diluents (e.g., sterile water), buffers, pharmaceutically acceptable excipients, and the like, packaged with or separately from the compounds described herein. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

Soluble CD73 kits and detection methods. In certain aspects, also provided herein are kits for determining the soluble CD73 (sCD73) in a sample. The kit includes an sCD73 capture antibody and a labeled sCD73 detection antibody. In some embodiments, the capture antibody is 7G2, Thermo Scientific #41-0200. In some embodiments, the labeled sCD73 detection antibody is AD2 clone, BioLegend #344017.

In some embodiments, the labeled sCD73 detection antibody is a biotinylated antibody, and the kit further comprises streptavidin-horseradish peroxidase, and a horseradish peroxidase substrate that is detectable after enzymatic conversion by the horseradish-peroxidase. In some embodiments, the horseradish peroxidase substrate is 3,3',5,5'-tetramethyibenzidine (TMB) or 2,2'-azino-di-[3-ethylbenzthiazoline-6-sulfonic acid] (ABTS).

In some embodiments the kit further comprises one or more of a coating buffer, a wash buffer, and a blocking buffer. In some embodiments the kit further comprises, a blocking buffer. In some embodiments, the kit further comprises a coating buffer. In some embodiments, the kit further comprises a wash buffer. In some embodiments, the coating buffer comprises about 0.2 M NaHCO$_3$ buffer, pH 9.6. In some embodiments, the wash buffer comprises about 0.1% Tween20 in PBS. In some embodiments, the blocking buffer comprises about 0.02% Tween20 in PBS+1% bovine serum albumin+10 µg/ml bovine IgG+10 µg/ml mouse IgG.

In further aspects also provided herein are methods for measuring amount of soluble CD73 (sCD73) in a sample. The methods include,
  a) contacting a sample with an immobilized anti-CD73 antibody to form a captured sCD73;
  b) contacting the captured sCD73 with a labeled anti-CD73 antibody to form a sandwiched sCD73, wherein the labeled anti-CD73 antibody binds to a different portion of the sCD73 than the immobilized anti-CD73 antibody;
  c) contacting the sandwiched sCD73 with an imaging solution to create a detectable signal
  d) measuring the detectable signal.

In some embodiments, the capture antibody is 7G2, Thermo Scientific #41-0200. In some embodiments, the labeled sCD73 detection antibody is AD2 clone, BioLegend #344017.

Step a) includes an incubation time to form the captures sCD73 complex between the immobilized anti-CD73 antibody and the sCH73 in the sample. This can be anywhere from a few minutes, about an hour, 2, 3, 4, 5, 6, 7, or 8 or more hours, or overnight. Longer times are also allowable. Like step a), step b) includes an incubation time that can range from a few minutes, about an hour, 2, 3, 4, 5, 6, 7, or 8 or more hours, or overnight. In some embodiments, the incubation time of step b) is about an hour. Similar to steps a) and b), step c) also includes an incubation time that can range from a few minutes, about an hour, 2, 3, 4, 5, 6, 7, or 8 or more hours, or overnight. In some embodiments, the incubation time of step c) is about an hour.

In some embodiments, the method further comprises one or more washing steps with a wash buffer after step a), step b), and step c). Washing is typically performed after the desired incubation time. In some embodiments, the wash buffer comprises about 0.1% Tween20 in PBS.

In some embodiments, the method further comprises a blocking buffer. In some embodiments, the blocking buffer is included in the sample prior to step a). In some embodiments, the blocking buffer is also included with the labeled anti-CD73 antibody in step b). In some embodiments the blocking buffer is also included with the imaging solution in step c). In some embodiments, the blocking buffer comprises about 0.02% Tween20 in PBS+1% bovine serum albumin+10 µg/ml bovine IgG+10 µg/ml mouse IgG.

There are a number of imaging solutions that are useful in ELISA assays. The identity of the label of the labeled anti-CD73 antibody will determine the appropriate imaging solution. Typically imaging solutions include reagents or substrates that are fluorescent or chemiluminescent. For example, when the label of the labeled anti-CD73 antibody is biotin, the imaging solution generally includes avadin or streptavidin that is conjugated to a fluorophore or to an additional agent that can combine to form a detectable signal or enzymatically convert a substrate into a detectable signal. In some embodiments, avadin or biotin is conjugated to horseradish peroxidase. Appropriate substrates for horseradish peroxidase (HRP) that form a signal when converted by HRP include 3,3',5,5'-tetramethylbenzidine (TMB) or 2,2'-azino-di-[3-ethylbenzthiazoline-6-sulfonic acid] (ABTS).

In some embodiments, the sample is blood. In some embodiments, the sample is serum isolated from blood samples. In some embodiments, the sample is plasma isolated from blood samples.

A person of skill in the art will recognize that the levels of different adenosine machinery proteins can be measured using similar sandwich ELISA methods.

Soluble adenosine monophosphate (AMP) hydrolytic activity kits and detection methods. In additional aspects, also provided herein are kits for determining the CD73 mediated and/or TNAP mediated adenosine monophosphate (AMP) hydrolytic activity in a sample. In some embodiments, a kit for determining the CD73 mediated adenosine monophosphate (AMP) hydrolytic activity in a sample comprises a CD73 inhibitor and AMP-Glo™. In some embodiments a kit for determining the TNAP mediated adenosine monophosphate (AMP) hydrolytic activity in a sample comprises a TNAP inhibitor and AMP-Glo™.

In some embodiments, the kits described herein further comprise an adenosine deaminase inhibitor, an SAH dehydrolase inhibitor, and an ADK inhibitor. These inhibitors can help decrease background adenosine degradation in a sample. In some embodiments, the adenosine deaminase inhibitor is EHNA. In some embodiments, the SAH dehydrolase inhibitor is aristromycin. In some embodiments, the ADK inhibitor is iodotubericidin.

In some embodiments, the kits further comprise adenosine monophosphate (AMP).

In further aspects also provided herein are methods for determining the CD73 mediated adenosine monophosphate (AMP) hydrolytic activity in a sample. The methods include,
  a) contacting a sample with a CD73 inhibitor, adenosine monophosphate (AMP), and AMP-Glo™ to form a CD73i sample;
  b) contacting a separate aliquot of the sample with adenosine monophosphate (AMP), and AMP-Glo™ to form a baseline sample;
  c) measuring an end RLU signal after a specified time period for the CD73i sample and the baseline sample; and
  d) assessing the difference between the end RLU for the CD73i sample and the baseline sample to determine the CD73 mediated AMP hydrolytic activity in a sample.

In further aspects also provided herein are methods for determining the TNAP mediated adenosine monophosphate (AMP) hydrolytic activity in a sample. The methods include,
  a) contacting a sample with a TNAP inhibitor, adenosine monophosphate (AMP), and AMP-Glo™ to form a TNAPi sample;
  b) contacting a separate aliquot of the sample with adenosine monophosphate (AMP), and AMP-Glo™ to form a baseline sample;
  c) measuring an end RLU signal after a specified time period for the TNAPi sample and the baseline sample; and d) assessing the difference between the end RLU for the TNAPi sample and the baseline sample to determine the TNAP mediated AMP hydrolytic activity in a sample.

In some embodiments, the CD73i sample, the TNAPi sample, and the baseline sample further comprise one or more of an adenosine deaminase inhibitor, an aristromycin dehydrolase inhibitor, and an ADK inhibitor. In some embodiments, the CD73i sample and/or the TNAPi sample further comprise an adenosine deaminase inhibitor, an SAH dehydrolase inhibitor, and an ADK inhibitor. In some embodiments, the adenosine deaminase inhibitor is EHNA. In some embodiments, the SAH dehydrolase inhibitor is aristromycin. In some embodiments, the ADK inhibitor is iodotubericidin.

The specified time period for measuring an end RLU signal is dependent on a number of factors. Chief among these is the amount of AMP included with the sample (step a and step b), since the RLU is a measurement of the AMP left over after the specified time period. When 25 µM AMP is used, reaction times on the order of minutes is usually sufficient to see a measurable change in signal. In some embodiments, the specified time period is 2, 3, 4, 5, 6, 7, 8, 9, 10, 11, 12, 13, 14, 15, or more minutes. In some embodiments, the specific time period is 8 minutes.

In some embodiments, the sample is blood. In some embodiments, the sample is blood serum. In some embodiments, the samples is blood plasma.

IV. EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Example 1—Determining the Amount of Soluble CD73 in Human Blood Via a Sandwich ELISA Methods for determining the amount of soluble CD73 in a human blood via a sandwich ELISA includes a capture antibody that coats the wells of a microtiter plate, a sample containing the analyte of interest, wash buffers, and a second biotin-conjugated antibody is used to detect the bound target. Secondary detection of the biotinylated antibody is accomplished using HRP-Streptavidin followed with a colorimetric or chemiluminescent substrate. Principles of the CD73 ELISA assay are outlined in FIG. 1.

Materials and Methods

Reagents and Equipment
  sCD73 capture antibody (7G2, Thermo Scientific #41-0200)
  Coating buffer:
    0.2 M NaHCO$_3$ buffer, pH 9.6 (Thermo Scientific #28382)
  Wash buffer:
    0.1% Tween20 in PBS
  Blocking Buffer:
    0.02% Tween20 in PBS+1% bovine serum albumin+10 µg/ml bovine IgG (Jackson ImmunoResearch #001-000-003)+10 µg/ml mouse IgG (Jackson ImmunoResearch #015-000-003)
  CD73 protein standards
  Biotinylated sCD73 detection antibody (AD2 clone, BioLegend #344017)
  Streptavidin-horseradish peroxidase (Thermo Scientific #21130)
  Chemiluminescence ELISA reagent (Thermo Scientific #37069)
  96 well microtiter plates, flat bottom, white, high-binding polystyrene (Costar #3922)
  Adhesive foil seals for plates
  EnVision Plate Reader
Protocol
  Coating Plates:
    1. Coat wells of microtiter plate with anti-sCD73 mAb (2 µg/ml, 100 µl) at 4° C. overnight. Seal plate for incubation.
    2. Wash wells four times with 0.1% Tween 20 in PBS (Tween/PBS, 350 µl each wash).
    3. Block with blocking buffer (200 µl) for at least 4 hr at room temperature.
    4. Wash wells four times.
  Use plate immediately, or seal tightly with wash buffer in the wells and store at 4° C.
  ELISA Assay:
    1. Dilute each sample in blocking solution (or create dilution series for samples and standards), then add each sample (100 µl) into the wells.
    2. Seal plate and incubate at 4° C. overnight.
    3. Wash wells four times.
    4. Add biotinylated anti-CD73 mAb (0.5 µg/ml, 100 µl in the blocking solution).
    5. Seal plate and incubate at room temperature for 1 h.
    6. Wash wells four times.
    7. Add streptavidin-horseradish peroxidase (100 µl, diluted 1:10000 in the blocking solution) into the wells.
    8. Incubate at room temperature again for 1 h.
    9. Wash wells four times.
    10. Develop with chemiluminescence ELISA reagent according to the manufacturer's instructions.
      a. Mix equal parts Luminol/Enhancer and Stable Peroxide Solution (solution is stable for 24 hr at RT—store in the dark).
      b. Add 100 µl of working solution to each well.
      c. Spin plate(s) at 1000× g for 2 minutes to remove all bubbles.
      d. Measure the intensities of the chemiluminescence reactions in the wells with a luminometer (1-5 min range is optimal).
Data Analysis Raw luminescence data from the EnVision Plate Reader is interpolated against a standard curve to determine absolute sCD73 levels. Concentration in each undiluted sample is calculated from all wells in a dilution series and these values are compared to each other to assess dilution linearity.

Figure 2A:
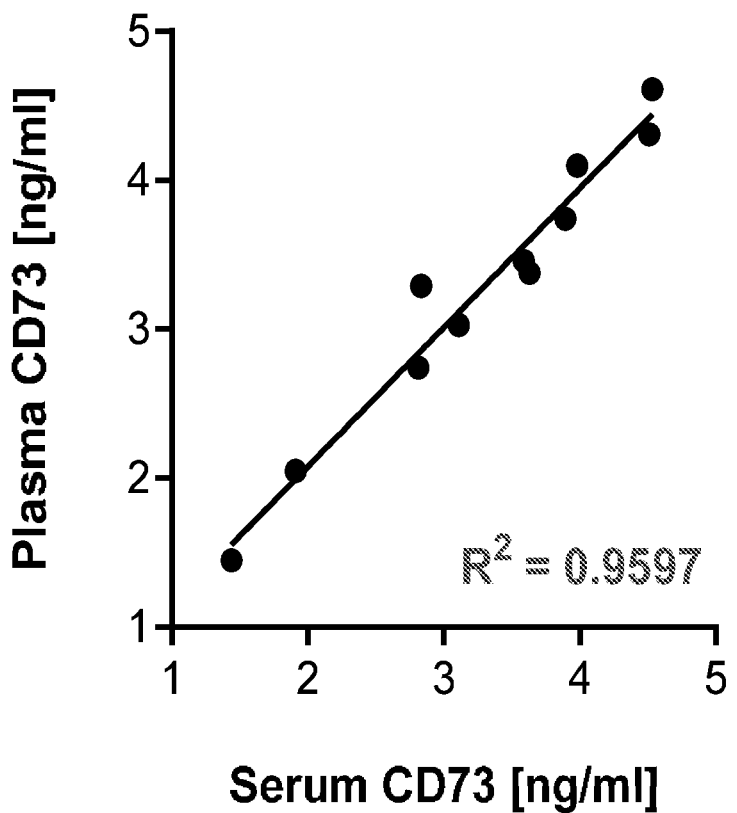
FIG. 2A-C A Robust Assay to Quantify Soluble CD73 in peripheral blood. (A) plots soluble CD73 concentrations in plasma versus serum from healthy donors showing a strong correlation; (B) plots a parallelism assessment identifying the quantitative range of the assay; (C) plots the soluble CD73 levels of healthy subjects and subjects with cancer showing that, in general, the soluble CD73 levels are elevated in cancer patients.
Figure 2B:
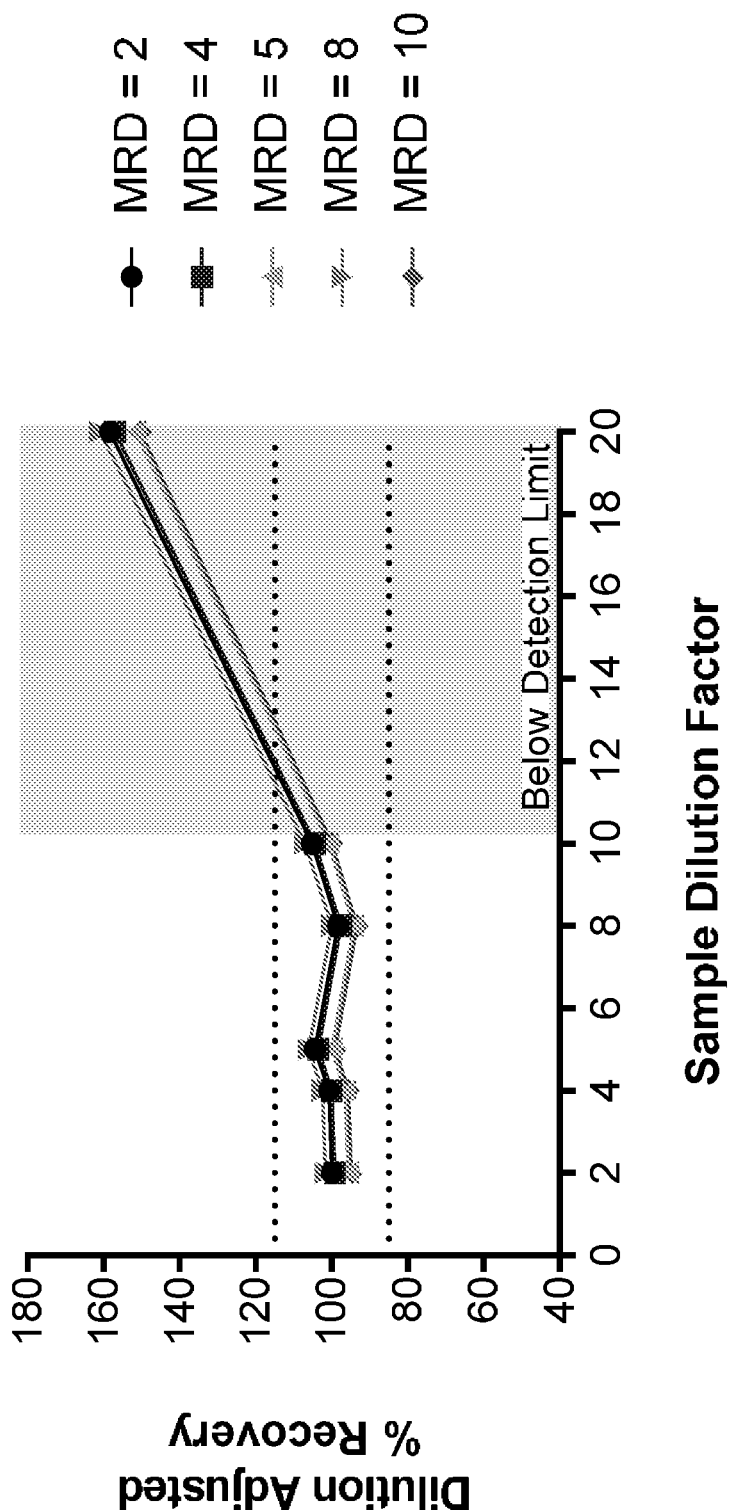
Figure 2C:
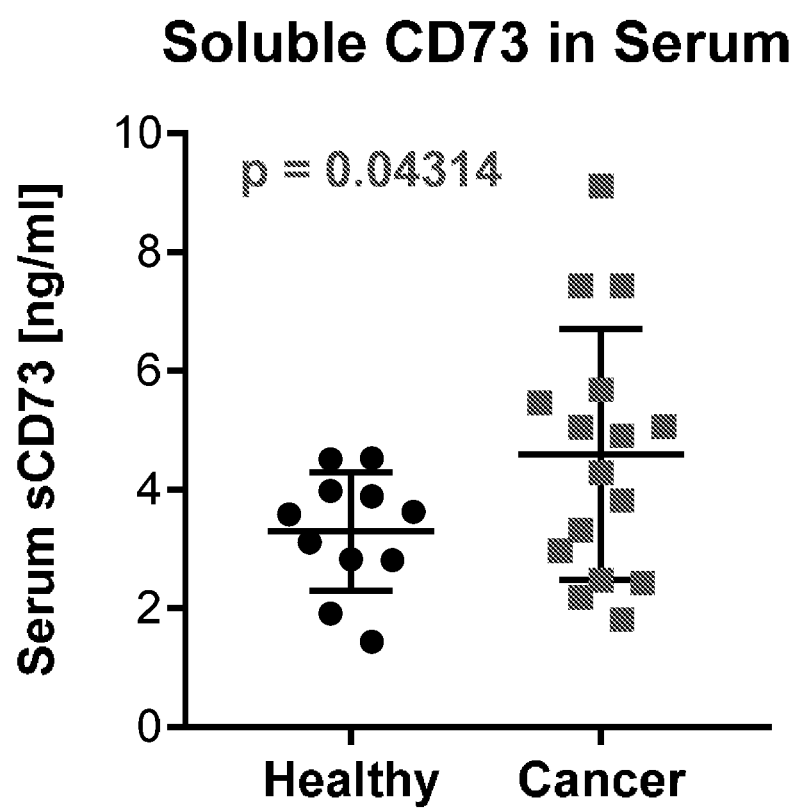

Using the assay described above, serum and sodium heparin plasma from health donors were evaluated to measure soluble CD73. As shown in FIG. 2A, the measurements were highly correlated. To determine the quantitative range of the assay, parallel assessment of samples were performed. FIG. 2B shows that this assay demonstrates acceptable assay parallelism. FIG. 2C shows a comparison of serum sCD73 between healthy subject and subjects with cancer. CD73 levels were generally higher in cancer patients than in health donors.

Figure 3A:
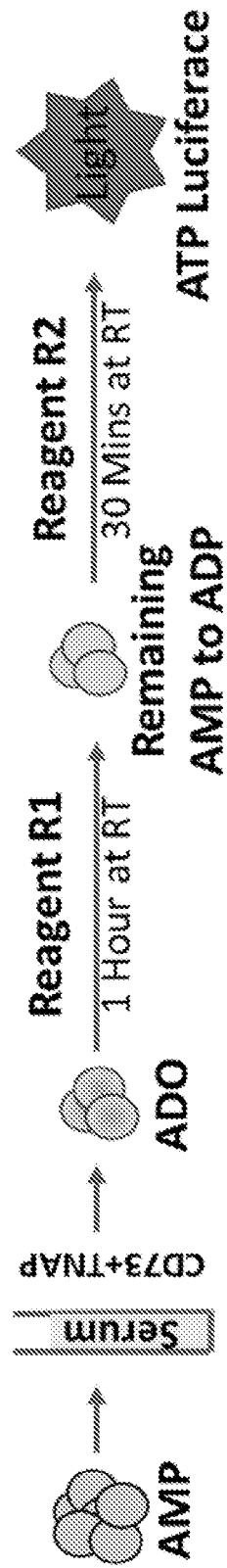
FIG. 3A-C Determination of AMP hydrolysis in Serum using AMP-Glo™. (A) shows a schematic summarizing the principles of the assay; (B) plots AMP hydrolysis in healthy volunteer serum under different conditions (+/−a CD73 inhibitor and/or a TNAP inhibitor); (C) plots correlations between CD73 protein concentration and AMP hydrolysis activities of healthy volunteer and cancer patient serum.

Example 2—Determining the Amount of Soluble CD73 and/or TNAP in Human Blood Via a AMP-Glo Hydrolysis Assay The presently described assay allows for determining the amount of hydrolytic activity of AMP in a blood sample is due to CD73 and/or TNAP. This is achieved using an AMP-Glo™ assay in the presence of 25 µM of AMP, CD73 and/or a TNAP inhibitor. AMP-Glo™ is a homogenous biochemical assay that generates a luminescent signal from a biochemical reaction that produces AMP. The principle of the AMP Glo assay is outlined in FIG. 3A.

Materials and Methods

Reagents
    A CD73 Inhibitor (Compound A)
    AMP-Glo™ (Cat. No. V5011, Promega Corporation)
    PBS—Phosphate Buffer Saline (Cat No. 10010023, Gibco)
    TNAP Inhibitor Cocktail:
    625 µM TNAP Inhibitor (CAS 496014-13-2, Calbiochem)
    10 µM EHNA, Adenosine Deaminase inhibitor (Cat. No. E114-25 mg, Sigma)
    4 µM Aristromycin, SAH dehydrolase inhibitor (Cat. No. SC-233890, Chem Cruz)
    10 µM 5-Iodotubericidin, ADK Inhibitor (Cat. No. I100-SMG, Sigma)
Materials and Equipment
    96 well assay plate (Cat No. 3992, Corning)
    EnVision Reader
Determination of AMP Hydrolytic Activity in Human Serum Serum isolated from healthy volunteer and cancer patient whole blood was stored at −80° C. 50 µl of serum from each donor was transferred to 4=×500 ul aliquots. The samples are then labelled a-d with the following conditions: a) No Compound A, No TNAP Inhibitor cocktail, b) 10 µM Compound A, No TNAP Inhibitor cocktail, c) No Compound A, With TNAP Inhibitor cocktail, d) 10 µM Compound A, With TNAP Inhibitor cocktail. To conditions c and d, 1:200 of the TNAP Inhibitor cocktail is added (0.25 µL) while to conditions b and d (with 10 µM Compound A), 1:100 of a 1 mM Compound A solution is added (final concentration is 10 µM). The samples are then mixed and incubated at 37° C. for 1 hour prior to transferring the samples at 18 µL/well to a low volume 96 well AMP Glo™ assay plate containing 2 µL of a final concentration of 25 µM AMP. Using a multichannel pipette, the samples are mixed 6-10 times and incubated for 8 minutes at room temperature prior to stopping the reaction with 20 µL the kit provided R1 solution. The 8-minute time point was chosen following a series of experiments to determine the time-point post AMP Spike-in that provided the best window in the assay without the addition of the CD73 inhibitor in human serum. Once the samples are mixed with R1, pre-prepared R2 solution+the AMP glo reagent are added to the wells at 40 µL per well. The final reaction mixture is incubated for 30 minutes prior to reading on a Wallac EnVision Reader to measure luminesce.
Analysis of Data from the AMP Glo Assay Data from the AMP Glo assay can be analyzed in multiple ways. The raw data is in the form of Raw Luminescence Units (RLU) from the Envision Reader. The data can be presented as RLU values, percent of AMP Leftover (AMP leftover at the end of 8-minute reaction time compared to 0 minutes), hydrolytic activity (comparing the RLU in the test sample with the well that contained maximum CD73 inhibitor with and without TNAP Inhibitors).

Figure 3B:
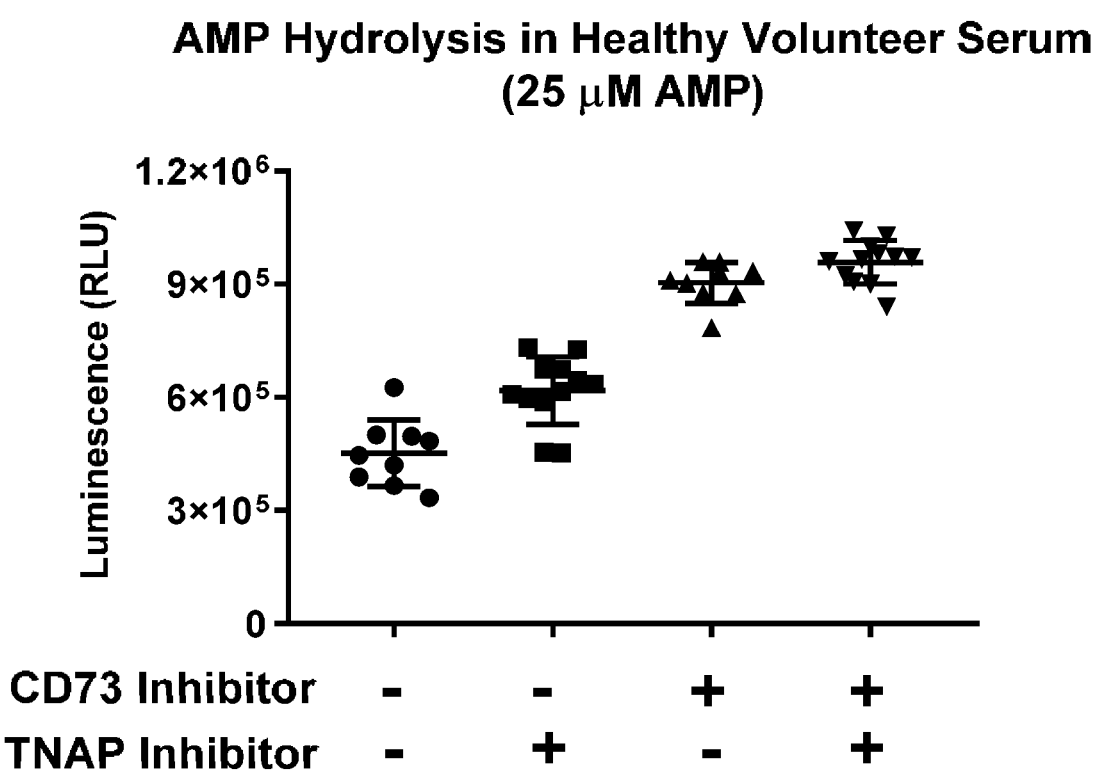
Figure 3C:
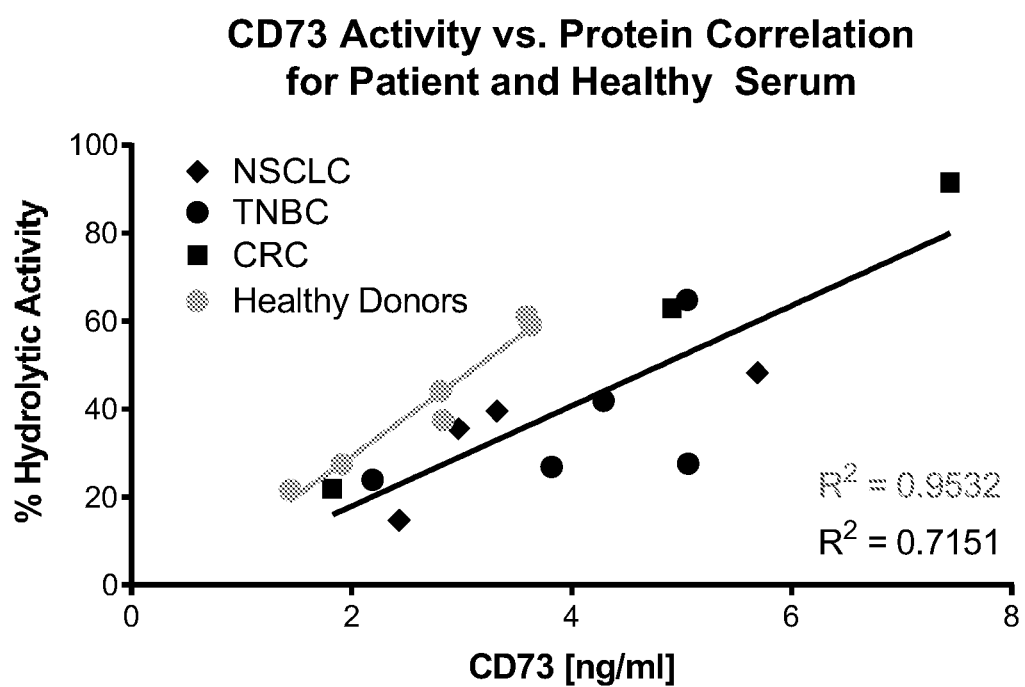
Figure 4A:
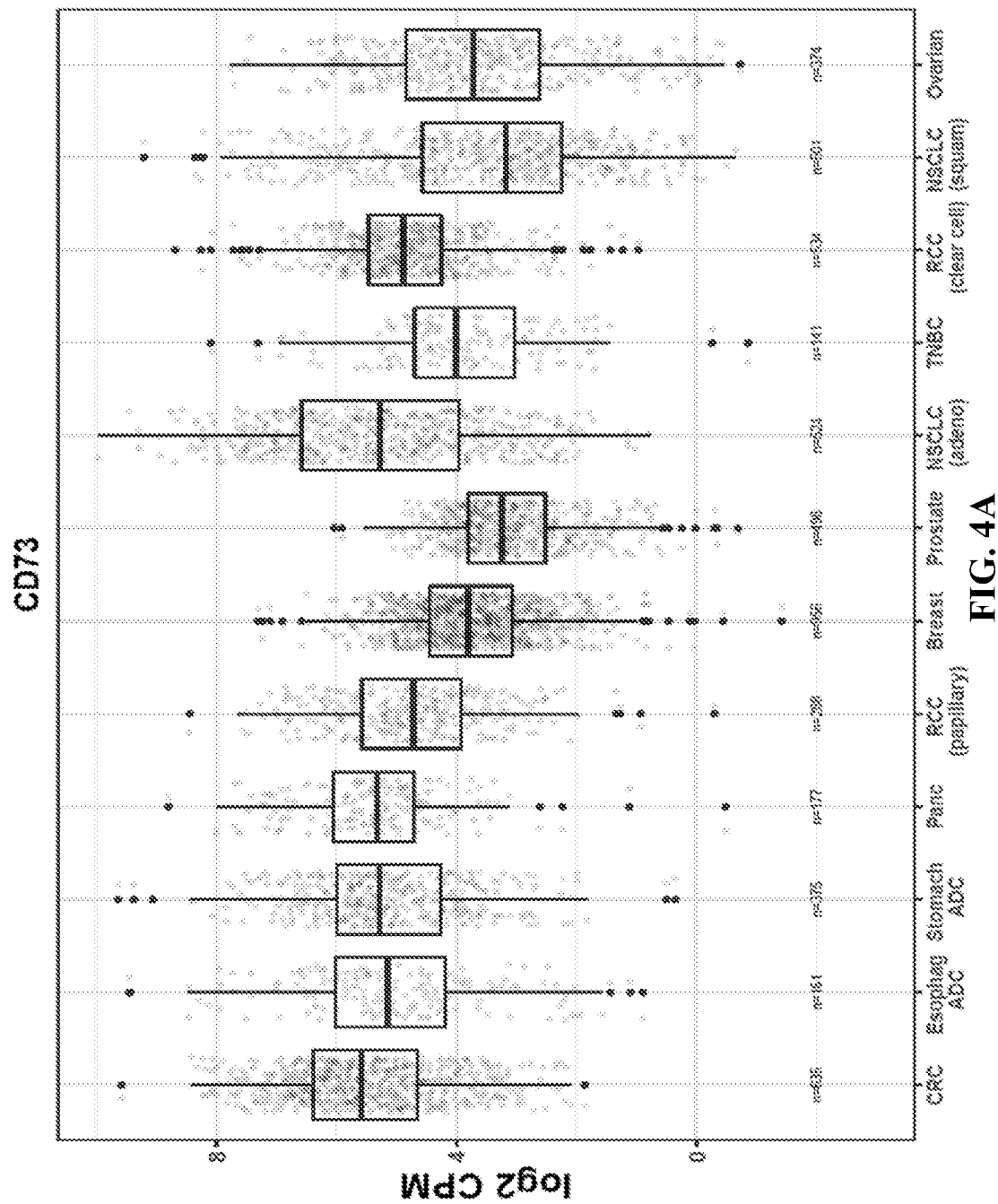
FIG. 4A-B TCGA Analysis of Human Tumors for CD73 and TNAP. CD73 (Panel A) and TNAP (Panel B) expression from RNAseq in The Cancer Genome Atlas samples are plotted. Numbers indicate the ratio of log 2 counts per million sample. Samples are ordered according to their CD73/TNAP ratio with higher CD73 expressing-tumors on the left and higher TNAP tumors on the right.
Figure 4B:
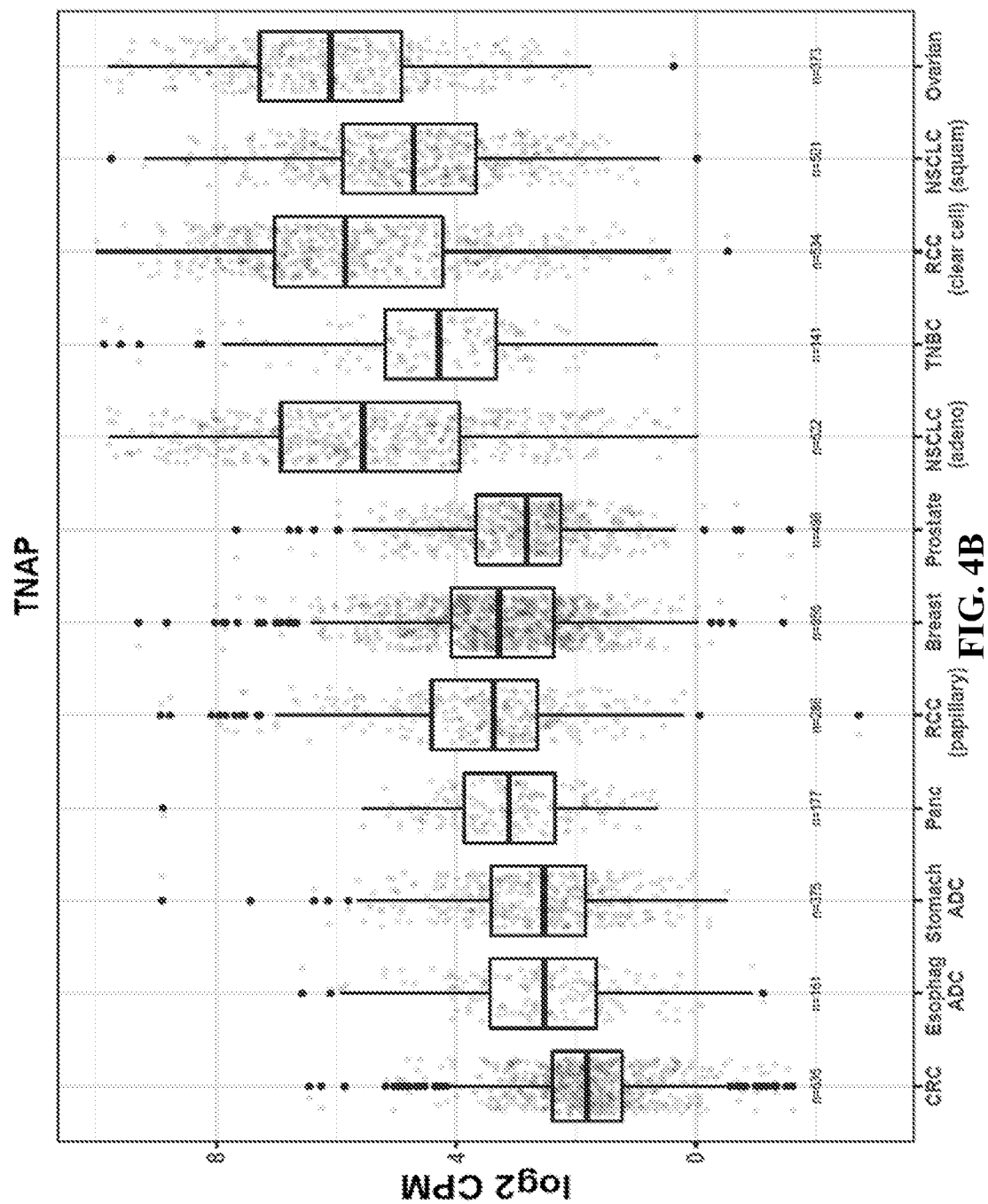

Using the assay described above, healthy volunteer serum was tested in the presence of CD73 and/or TNAP inhibitors, the luminescence (RLU) values measured are shown in FIG. 3B. A correlation between percent hydrolytic activity of CD73 and CD73 protein concentration in healthy subject and subjects with cancer are shown in FIG. 3C.

Example 3—Determining the Amount of CD73 and/or TNAP Using Immunostaining

Figure 5A:
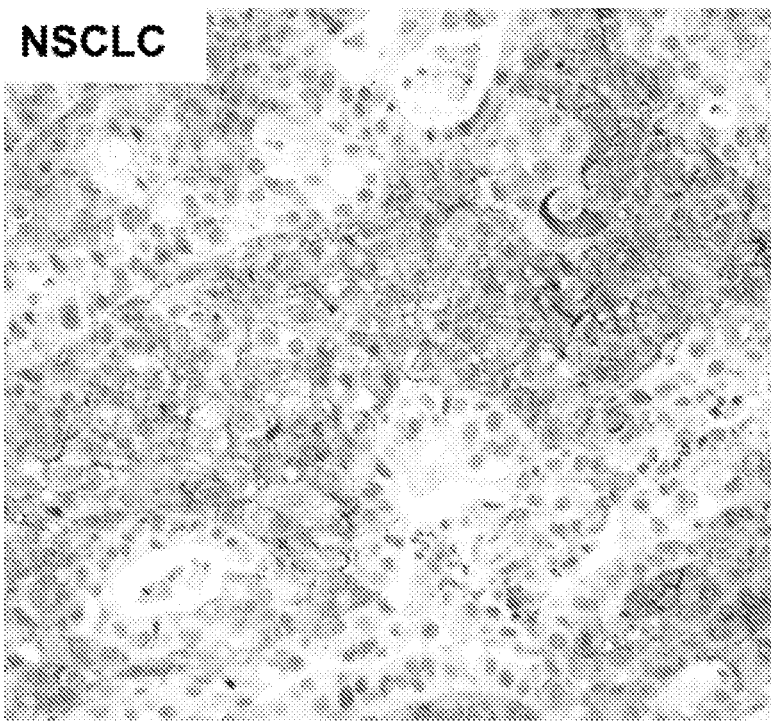
FIG. 5A-F Detecting and Quantifying CD73 in Human Tumors using Immunostaining. (A-D) show representative images of immunostaining for CD73 (brown) on human FFPE tumor samples. The displayed tumors are non-small-cell lung cancer (NSCLC) (A,B), triple-negative breast cancer (TNBC) (C), and colorectal cancer (CRC) (D); Panel E shows quantification of CD73 staining area as a percentage of total tumor area in the listed cancers; and Panel F plots the correlation between H-score and percent staining area.
Figure 5B:
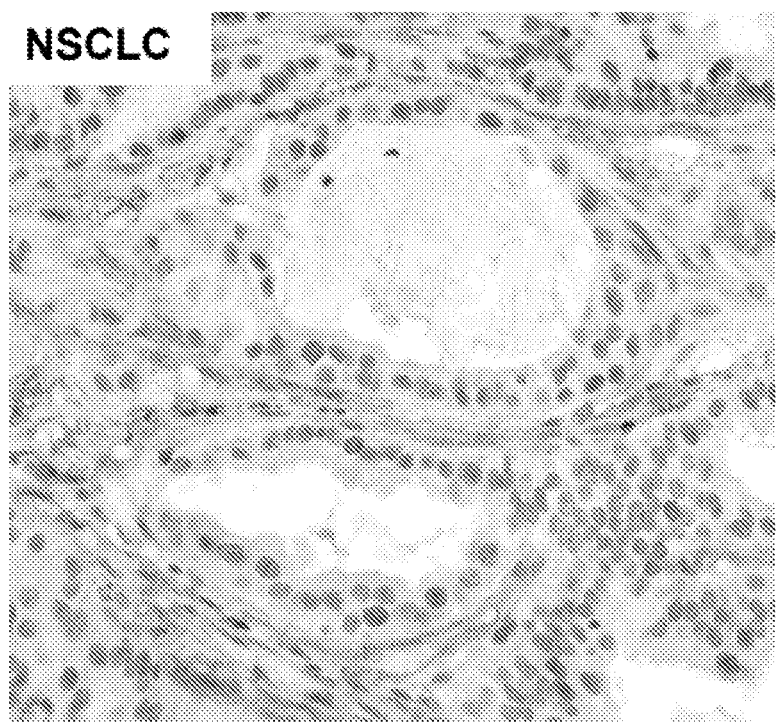
Figure 5C:
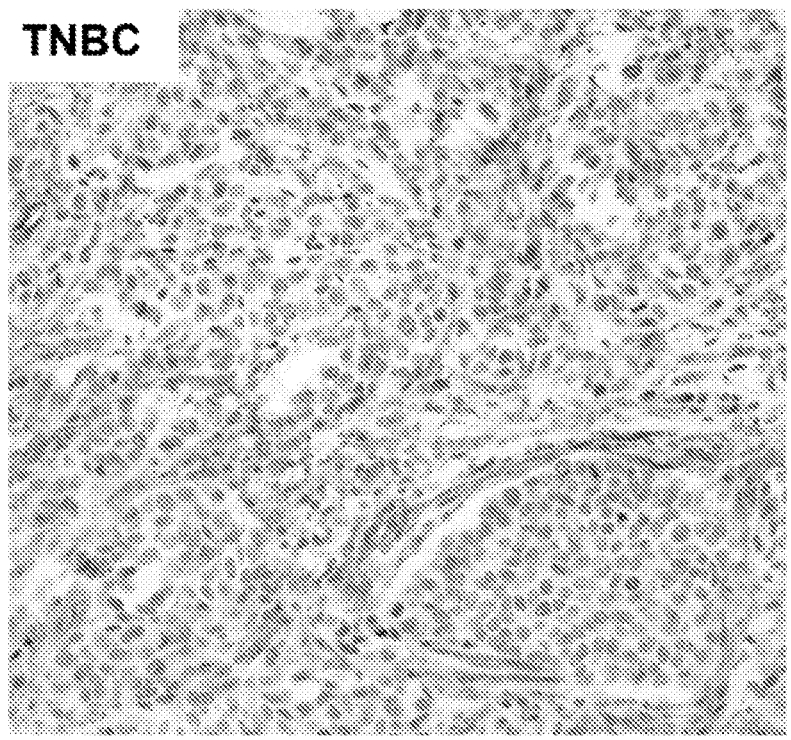
Figure 5D:
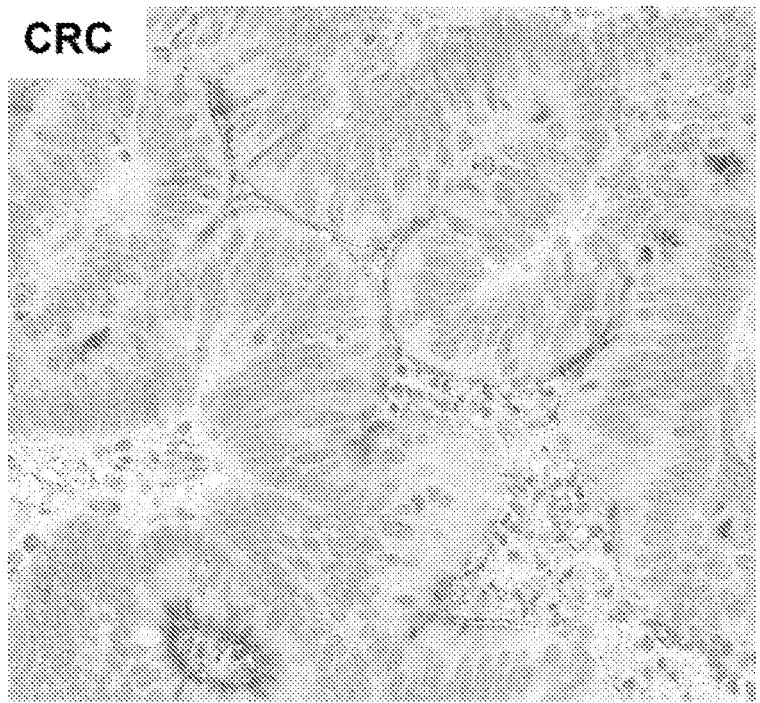
Figure 5E:
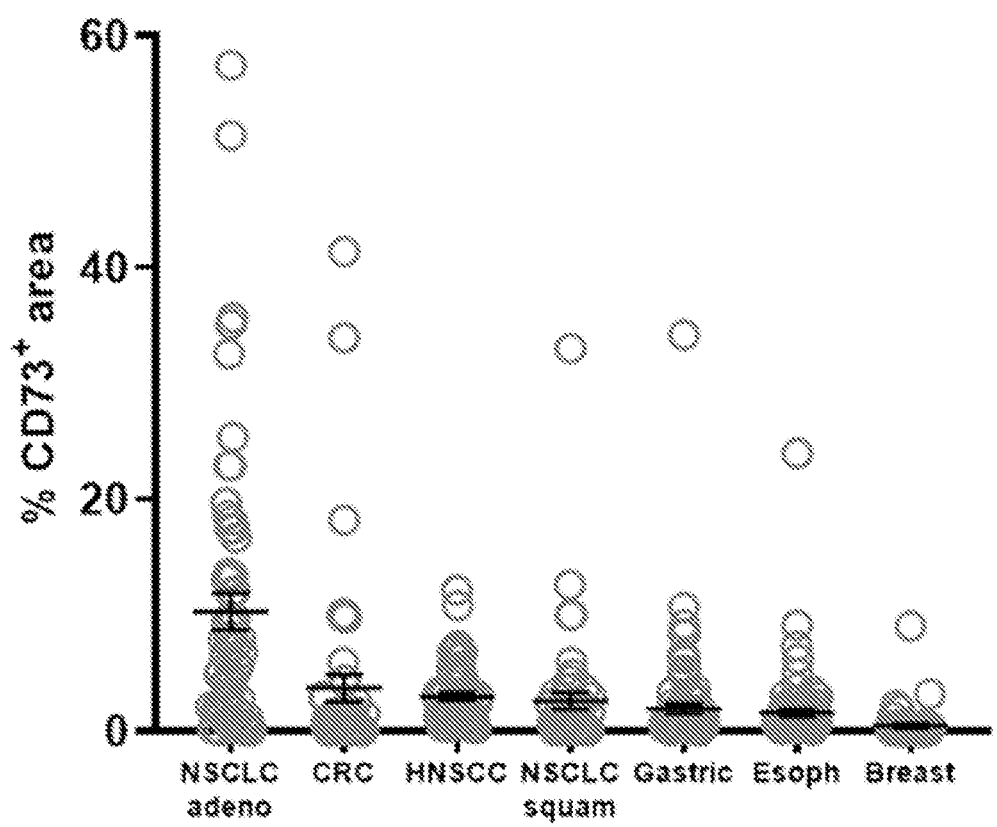
Figure 5F:
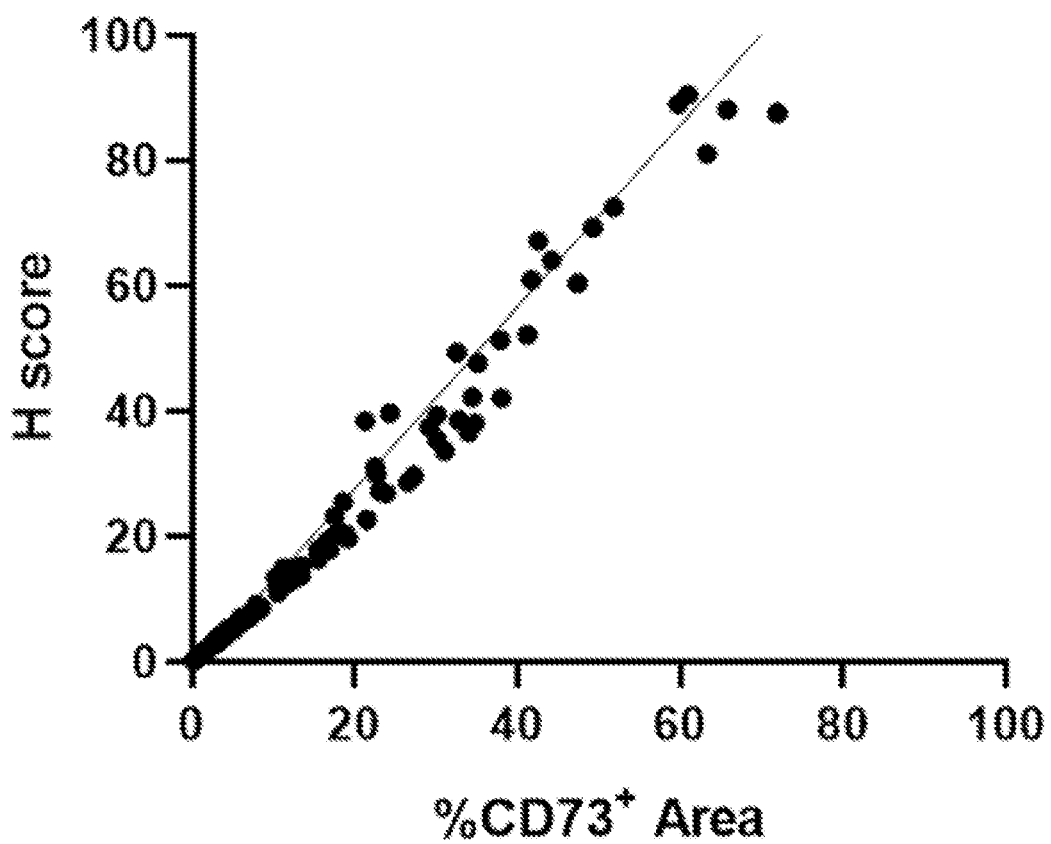
Figure 6A:
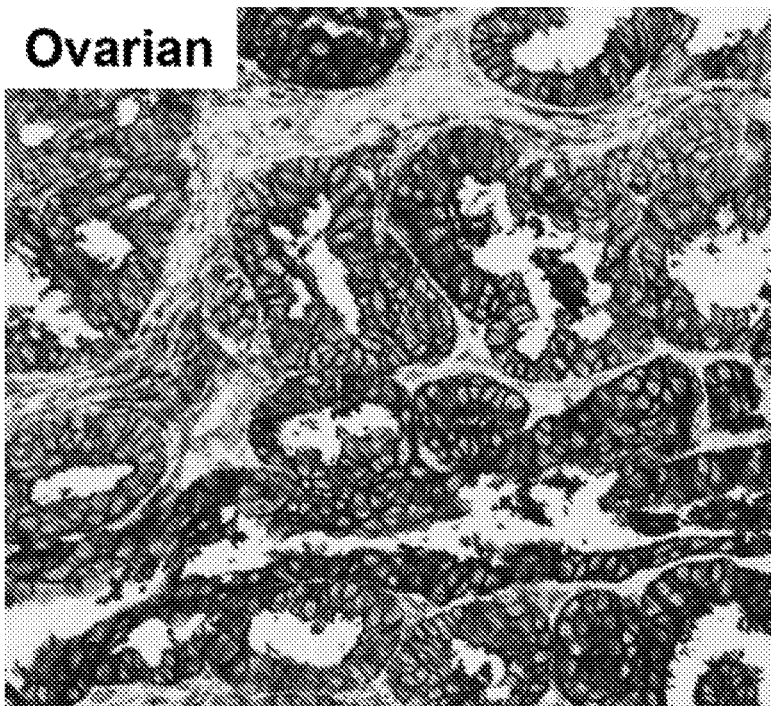
FIG. 6A-E Detecting and Quantifying TNAP in Human Tumors using Immunostaining. (A-D) show representative images of immunostaining for TNAP (brown) on human FFPE tumor samples. The displayed tumors are ovarian cancer (A), non-small-cell lung cancer (NSCLC) (B), breast cancer (C), and colorectal cancer (CRC) (D); Panel E shows quantification of TNAP staining area as a percentage of total tumor area in the listed cancers.
Figure 6B:
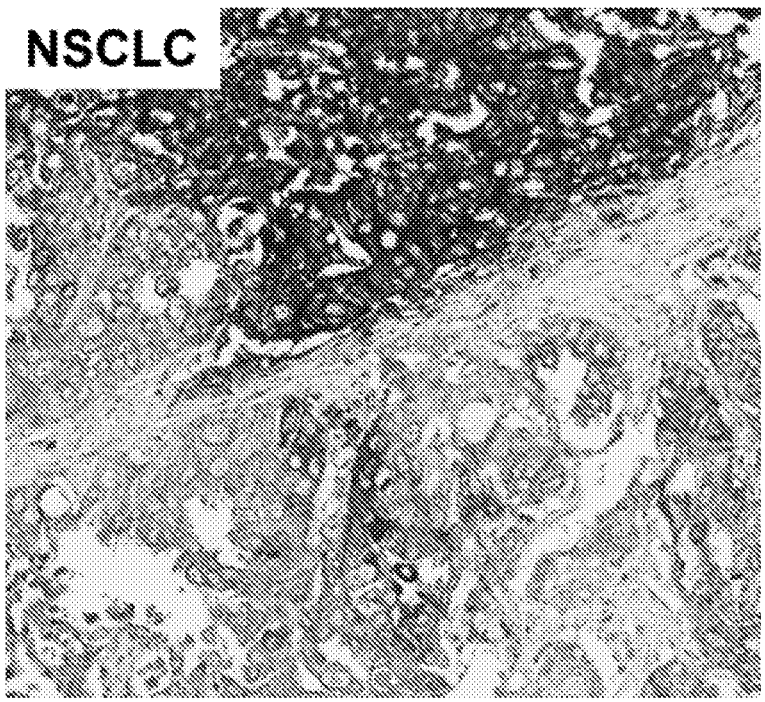
Figure 6C:
Figure 6D:
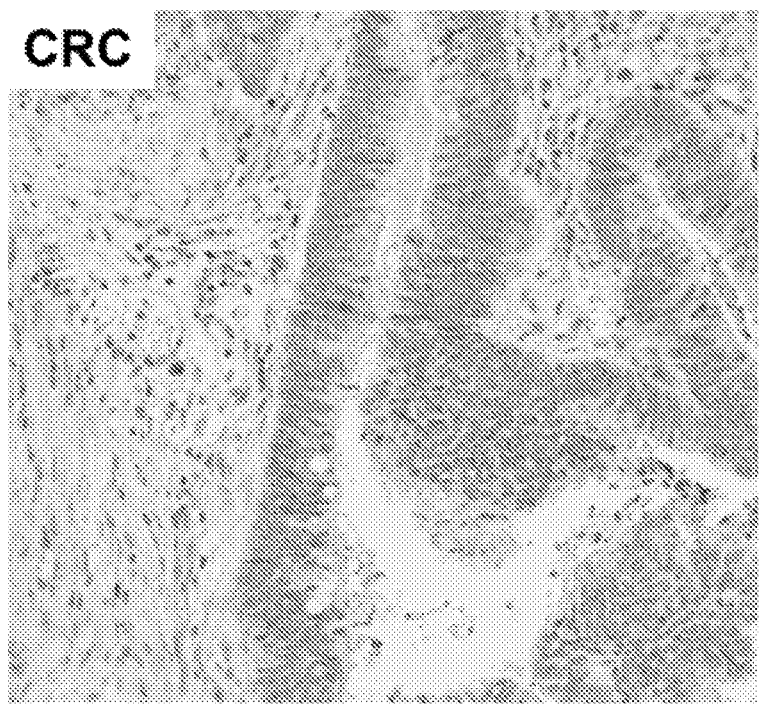
Figure 6E:
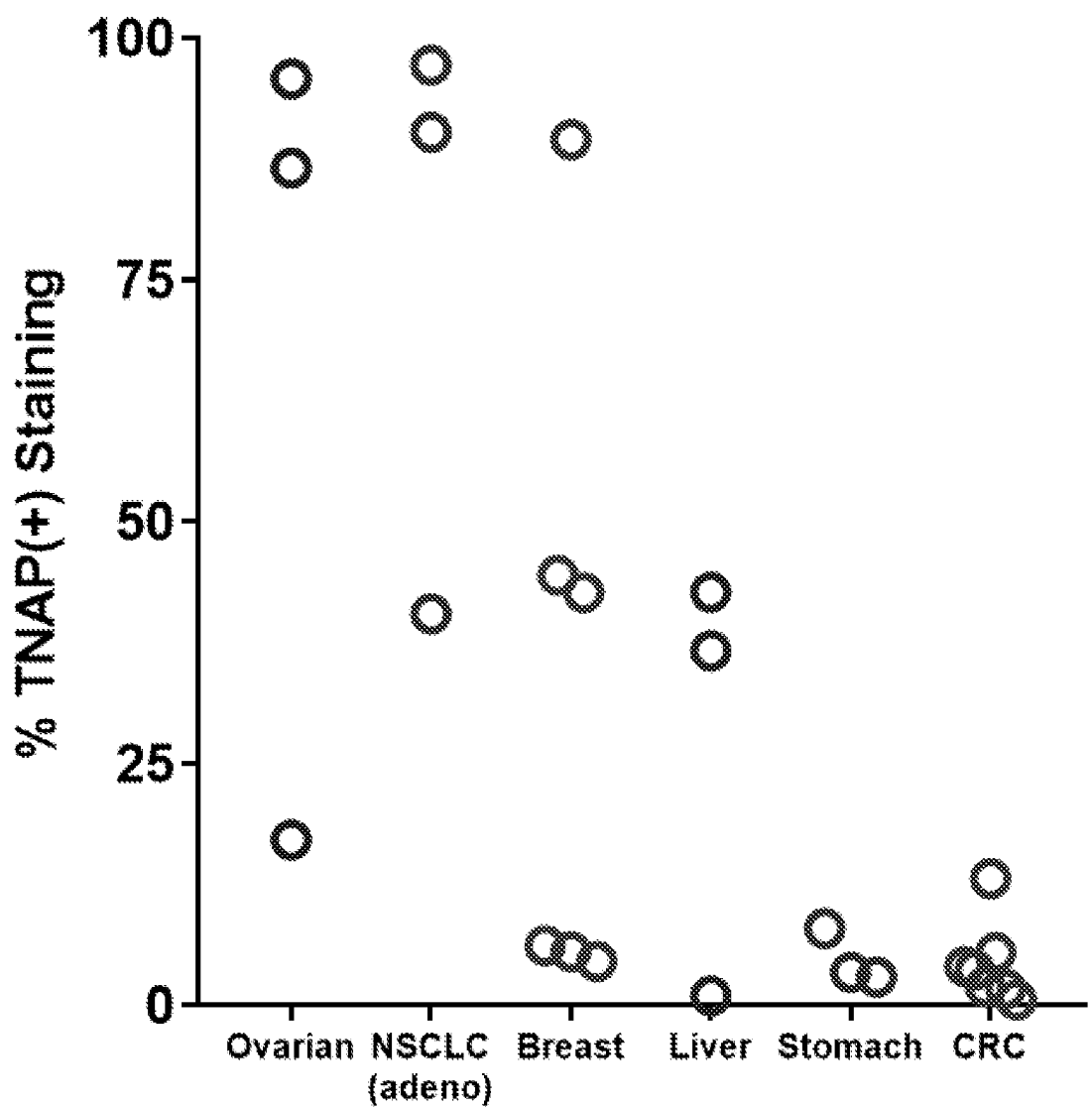

Ecto 5' Nucleotidase (CD73) and tissue non-specific alkaline phosphatase (TNAP) protein were detected in formalin fixed paraffin embedded (FFPE) tissue, following antigen retrieval, using the anti-NTSE/CD73 D7F9A antibody clone from Cell Signaling Technology and the anti-Anti-Alkaline Phosphatase/ALPL R034 antibody clone from Sino Biological. Detection for singleplex antibody stains was performed using an anti-rabbit IgG conjugated to horseradish peroxidase (HRP) and chromogenic deposition of 3,3'-diaminobenzidine (DAB). Simultaneous detection of both CD73 and TNAP was performed in a multiplex fluorescent assay using the antibody clones above and HRP was used to deposit a fluorescent chromogen. Calculations of positive staining area, percentage of positive staining cells, H-score, combined positive score (CPS), and tumor proportion score (TPS) were calculated using image analysis programs. For singleplex chromogenic staining, QuPath Quantitative Pathology & Bioimage Analysis programs were used. For the multiplex fluorescence, HALO software from Indica labs was used. FIGS. 5A-D and 6A-D show representative images of immunostaining for CD73 and TNAP, respectively. FIGS. 5E and 6E plot the quantification of staining area of CD73 and TNAP as a percentage of total tumor area. FIG. 5F plots the correlation between percent staining area and H-score.

Example 4—Determining the Amount of CD73, TNAP, or Other Adenosine Machinery mRNA RNA extraction from formalin fixed paraffin embedded (FFPE) tissue is performed using the Qiagen RNeasy FFPE kit (#73504). Tissue sections are either scraped from microscope slides using a scalpel or sections are placed directly into a microcentrifuge tube. NanoString analysis is performed with extracted RNA using the nCounter oncology or immunology panels on a nCounter SPRINT profiler then analyzed using the nSolver software package. Real-time PCR is performed on cDNA generated from the extracted FFPE RNA using Taqman probes on an Applied Biosystems QuantStudio 6 Flex Real-time PCR system.

Example 5—Determining the Tumor Mutation Burden (TMB) in a Subject

Methods for determining the tumor mutation burden (TMB) in a subject described herein are published in Goodman et al. Tumor Mutational Burden as an Independent Predictor of Response to Immunotherapy in Diverse Cancers. *Mol Cancer Ther*. (2017). 16(11):2598-2608.

Example 6—Determining the PD-L1 Status of a Subject

There are a number of methods known for determining the PD-L1 status of a subject. One useful method is through the use of the FDA approved PD-L1 IHC 22C3 pharmDx device and methods developed by Dako North America, Inc.

Example 7—Determining the Amount of CD73 and/or TNAP Using an Isotopic AMP Hydrolysis Assay Assay Design The activity of CD73 in human plasma was assessed in vitro using a LC-MS/MS method monitoring the dephosphorylation of $^{13}C_5$-AMP to $^{13}C_5$-adenosine. An inhibitor cocktail was used to block neuronal tissue-nonspecific alkaline phosphatase (TNAP) and to stabilize $^{13}C_5$-adenosine, which consisted of 2,5-dimethoxy-N-(quinolin-3-yl)benzenesulfonamide (a TNAP inhibitor), erythro-9-(2-hydroxy-3-nonyl)adenine (EHNA, an adenosine deaminase inhibitor), 5-iodotubercidin (an adenosine kinase inhibitor) and aristeromycin (a S-adenosyl-L-homocysteine hydrolase inhibitor).

$IC_{50}$ values were estimated by nonlinear regression analysis.

Assay Conditions

Human plasma (50 µL) at pH 7.4 was preincubated with a CD73 inhibitor (Compound A) (0 to 10 µM), and EHNA (10 µM), dimethoxy-N-(quinolin-3-yl)benzenesulfonamide (625 µM), 5-iodotubercidin (10 µM), and aristeromycin (4 µM) for 1 hour. The reaction was initiated with 5 µM $^{13}C_5$-AMP and was allowed to proceed for 1 min at 37° C. in a shaking water bath. The reactions were terminated by addition of four volumes of 0.4M perchloric acid containing an internal standard (cIMP, 5 ng/mL). The samples were vortexed for 15 minutes, and then centrifuged at 4,200 rpm for 20 minutes at 10° C. The supernatant was analyzed by LC-MS/MS as described under the analytical method section.

Analytical Methods & Data Analysis

Mass spectrometer acquisition and integration was performed with Applied Biosystems-Sciex Analyst software (version 1.6.3).

Instrument:
- API 4000 mass spectrometer (Applied Biosystems, Foster City, CA)
- API 6500 mass spectrometer (Applied Biosystems, Foster City, CA)
- Shimadzu Nexera X2 UHPLC System (Shimadzu Scientific Instruments, Canby, OR)
- Column: Atlantis dC18, 100 Å, 3.0×100 mm, 3 µm (Waters, Milford, MA)
- Injection Volume: 0.5 µL
- Flow Rate: 0.80 mL/min HPLC Gradient:

| Time (min) | Mobile Phase A<br>10 mM ammonium formate and 0.1% formic acid in water | Mobile Phase B<br>10 mM ammonium formate in 95% acetonitrile, 5% water |
| --- | --- | --- |
| 0 | 99 | 1 |
| 1.0 | 92 | 8 |
| 2.0 | 5 | 95 |
| 2.8 | 5 | 95 |
| 2.9 | 99 | 1 |
| 4.2 | 99 | 1 |

Ionization Mode: Electrospray (ESI)

Detection Mode: Positive MRM (Q1/Q3 transitions: m/z 273.14/136.10 for $^{13}C_5$-adenosine; m/z 330.98/137.10 for cIMP)

Analysis of the sample without the CD73 inhibitor provides information on the activity of CD73 in the sample. Performing the same assessment with a CD73 inhibitor and/or a TNAP inhibitor allows for assessment of the relative contributions of CD73 versus TNAP mediated dephosphorylation of AMP.

Using the titration of CD73 inhibitor, $IC_{50}$ values were estimated by fitting data to the following 4-parameter equation (with variable slope), using the algorithms contained in GraphPad Prism Version 5.0 (GraphPad Software Inc., San Diego, CA):

$$\% \text{ activity} = \min + \frac{(\max - \min)}{(1 + 10^{(logIC50 - log[I])HillSlope})}$$

Figure 7A:
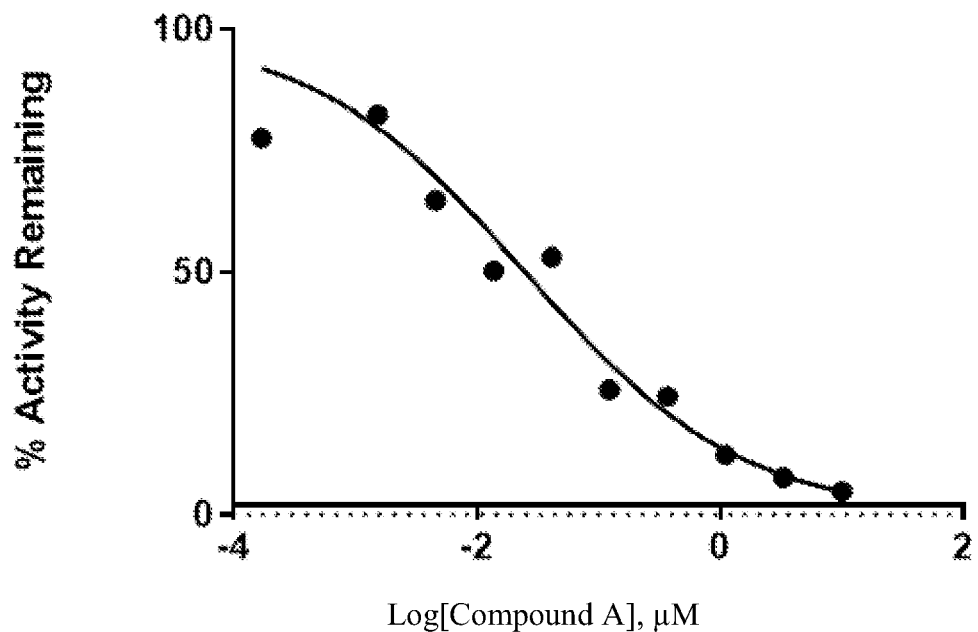
FIG. 7A-C Inhibition of CD73-Mediated Dephosphorylation of $^{13}C_5$-AMP to $^{13}C_5$-Adenosine in Human Plasma. (A-C) show representative plots of the percent activity remaining at certain tested concentrations of Compound A. The data points and plots shown were used to calculate the $IC_{50}$ for Volunteer 1 (Panel A), Volunteer 2 (Panel B), and Volunteer 3 (Panel C).
Figure 7B:
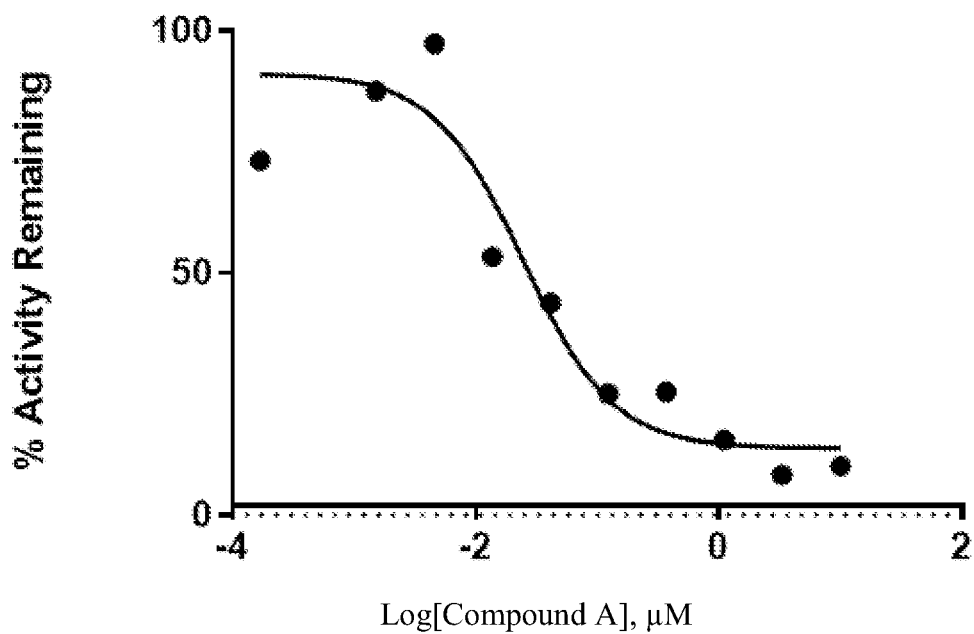
Figure 7C:
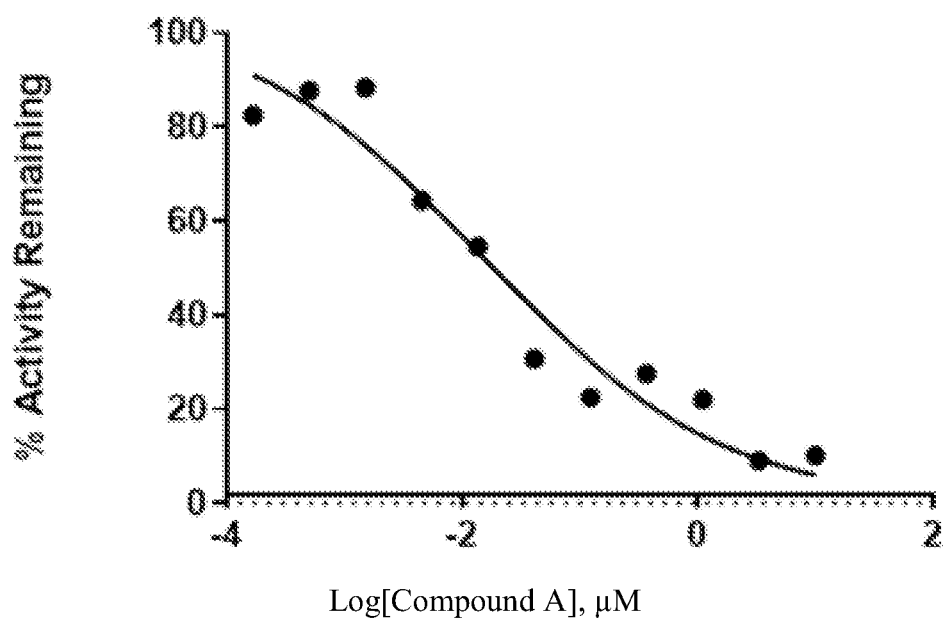

Representative $IC_{50}$ values from two volunteers are shown in Table 1 below as well as FIG. 7A-C.

TABLE 1

Inhibitory Potency of Compound A Against CD73 in Human Plasma ($IC_{50}$)

| Plasma ID | $IC_{50}$ (nM) |
| --- | --- |
| Volunteer 1 | 24.8 |
| Volunteer 2 | 25.0 |
| Volunteer 3 | 15.4 |

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A method of inhibiting or suppressing a cancer in a subject in need thereof comprising administering to the subject a therapeutically effective amount of a CD73 inhibitor,
   wherein the cancer has an established adenosine fingerprint determined from a biopsy from the subject,
   wherein the established adenosine fingerprint is an increase in the amount of CD73 as determined by immunostaining for CD73,
   wherein the increase in the amount of CD73 as determined by immunostaining is a measured value above a threshold value that is a CD73 staining of 1% or more of cancer cells in the biopsy or a measured value above an average value of CD73 immunostaining in biopsy samples from a population of subjects with the same type of cancer, and
wherein the CD73 inhibitor is Compound A

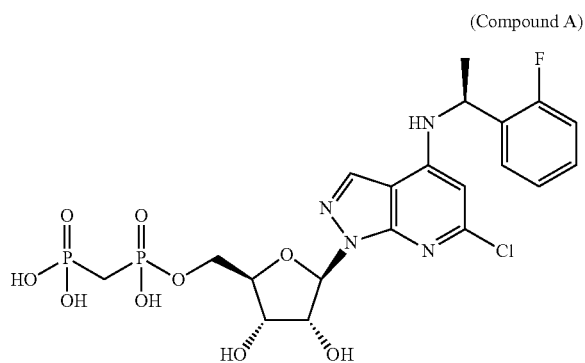 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

(Compound A)

or a pharmaceutically acceptable salt thereof.

2. The method of claim 1, wherein the increase in the amount of CD73 as determined by immunostaining is calculated as positive staining area, percentage of positive staining cells, H-score, combined positive score, or tumor proportion score.

3. The method of claim 1, wherein the increase in the amount of CD73 as determined by immunostaining is a measured value above the average value of CD73 immunostaining in biopsy samples from a population of subjects with the same type of cancer.

4. The method of claim 1, wherein the increase in the amount of CD73 as determined by immunostaining is a measured value above a threshold value, that is a CD73 staining of 1% or more of cancer cells in the biopsy.

5. The method of claim 1, wherein the cancer is a cancer of the prostate, colon, rectum, pancreas, cervix, stomach, endometrium, brain, liver, bladder, ovary, testis, head, neck, skin, mesothelial lining, white blood cell, esophagus, breast, muscle, connective tissue, lung, adrenal gland, thyroid, kidney, or bone, or the cancer is glioblastoma, mesothelioma, renal cell carcinoma, gastric carcinoma, sarcoma, choriocarcinoma, cutaneous basocellular carcinoma, or testicular carcinoma.

6. The method of claim 1, further comprising administering to the subject a PD1 inhibitor and/or a PD-L1 inhibitor.

7. The method of claim 6, wherein the PD1 and/or PD-L1 inhibitor is selected from the group consisting of pembrolizumab, nivolumab, MEDI-0680, BGB-108, GB-226, PDR-001, mDX-400, SHR-1210, IBI-308, PF-06801591, atezolizumab, durvalumab, avelumab, BMS-936559, KD-033, CA-327, CA-170, ALN-PDL, TSR-042, and STI-1014.

8. The method of claim 1, further comprising a chemotherapeutic agent, wherein the chemotherapeutic agent comprises a platinum-based or anthracycline-based chemotherapeutic agent.

* * * * *